US010968981B2

(12) United States Patent
Nicholas

(10) Patent No.: US 10,968,981 B2
(45) Date of Patent: Apr. 6, 2021

(54) ELECTROMECHANICAL SURGICAL DEVICES WITH SINGLE MOTOR DRIVES AND ADAPTER ASSEMBLIES THERFOR

(71) Applicant: Covidien LP, Mansfield, MA (US)

(72) Inventor: David Nicholas, Trumbull, CT (US)

(73) Assignee: COVIDIEN LP, Mansfield, MA (US)

( * ) Notice: Subject to any disclaimer, the term of this patent is extended or adjusted under 35 U.S.C. 154(b) by 191 days.

(21) Appl. No.: 16/295,547

(22) Filed: Mar. 7, 2019

(65) Prior Publication Data

US 2019/0203805 A1 Jul. 4, 2019

Related U.S. Application Data

(63) Continuation of application No. 15/368,869, filed on Dec. 5, 2016, now Pat. No. 10,253,847.

(Continued)

(51) Int. Cl.

| | |
|---|---|
| ***F16H 1/22*** | (2006.01) |
| ***A61B 17/28*** | (2006.01) |
| ***A61B 17/072*** | (2006.01) |
| ***A61B 17/10*** | (2006.01) |
| ***F16H 25/18*** | (2006.01) |

(Continued)

(52) U.S. Cl.

CPC ............ *F16H 1/22* (2013.01); *A61B 17/072* (2013.01); *A61B 17/07207* (2013.01); *A61B 17/10* (2013.01); *A61B 17/28* (2013.01); *F16H 25/18* (2013.01); *A61B 2017/00017* (2013.01); *A61B 2017/0046* (2013.01); *A61B 2017/00221* (2013.01); *A61B 2017/00393* (2013.01); *A61B 2017/00398* (2013.01); *A61B 2017/00464* (2013.01); *A61B 2017/00473* (2013.01); *A61B 2017/00477* (2013.01); *A61B 2017/00734* (2013.01); *A61B 2017/2927* (2013.01)

(58) Field of Classification Search

CPC ................................ F16H 1/22; A61B 17/28
USPC ...................................................... 74/665 F
See application file for complete search history.

(56) References Cited

U.S. PATENT DOCUMENTS

| | | | |
|---|---|---|---|
| 2,777,340 | A | 1/1957 | Hettwer et al. |
| 2,957,353 | A | 10/1960 | Babacz |

(Continued)

FOREIGN PATENT DOCUMENTS

| | | | |
|---|---|---|---|
| CA | 2451558 | A1 | 1/2003 |
| CN | 1547454 | A | 11/2004 |

(Continued)

OTHER PUBLICATIONS

Extended European Search Report corresponding to counterpart International Application No. EP 14 18 4882.0 dated May 12, 2015.

(Continued)

*Primary Examiner* — Ha Dinh Ho
(74) *Attorney, Agent, or Firm* — Carter, DeLuca & Farrell LLP

(57) ABSTRACT

The present disclosure relates to surgical systems including hand-held electromechanical surgical devices and adapter assemblies for connecting surgical loading units to the hand-held electromechanical surgical devices. The presently described electromechanical surgical devices include single motor drives that selectively drive various output assemblies coordinated by selector motors to operate the surgical loading units.

20 Claims, 24 Drawing Sheets

120 124a 124 124f 124b 126 "A" 122e 124c 140 130b 128 122 122a 124e 124c 124d 122c 122b 122d 130 130c 130a

Related U.S. Application Data

(60) Provisional application No. 62/270,804, filed on Dec. 22, 2015.

(51) Int. Cl.
*A61B 17/00* (2006.01)
*A61B 17/29* (2006.01)

(56) References Cited

U.S. PATENT DOCUMENTS 3,111,328 A 11/1963 Di Rito et al.
3,695,058 A 10/1972 Keith, Jr.
3,734,515 A 5/1973 Dudek
3,759,336 A 9/1973 Marcovitz et al.
4,162,399 A 7/1979 Hudson
4,606,343 A 8/1986 Conta et al.
4,705,038 A 11/1987 Sjostrom et al.
4,722,685 A 2/1988 de Estrada et al.
4,823,807 A 4/1989 Russell et al.
4,874,181 A 10/1989 Hsu
5,129,118 A 7/1992 Walmesley
5,129,570 A 7/1992 Schulze et al.
5,152,744 A 10/1992 Krause et al.
5,301,061 A 4/1994 Nakada et al.
5,312,023 A 5/1994 Green et al.
5,326,013 A 7/1994 Green et al.
5,350,355 A 9/1994 Sklar
5,383,874 A 1/1995 Jackson et al.
5,383,880 A 1/1995 Hooven
5,389,098 A 2/1995 Tsuruta et al.
5,395,033 A 3/1995 Byrne et al.
5,400,267 A 3/1995 Denen et al.
5,411,508 A 5/1995 Bessler et al.
5,413,267 A 5/1995 Solyntjes et al.
5,427,087 A 6/1995 Ito et al.
5,433,721 A 7/1995 Hooven et al.
5,467,911 A 11/1995 Tsuruta et al.
5,476,379 A 12/1995 Disel
5,487,499 A 1/1996 Sorrentino et al.
5,518,163 A 5/1996 Hooven
5,518,164 A 5/1996 Hooven
5,526,822 A 6/1996 Burbank et al.
5,529,235 A 6/1996 Boiarski et al.
5,535,934 A 7/1996 Boiarski et al.
5,535,937 A 7/1996 Boiarski et al.
5,540,375 A 7/1996 Bolanos et al.
5,540,706 A 7/1996 Aust et al.
5,542,594 A 8/1996 McKean et al.
5,549,637 A 8/1996 Crainich
5,553,675 A 9/1996 Pitzen et al.
5,562,239 A 10/1996 Boiarski et al.
5,564,615 A 10/1996 Bishop et al.
5,609,560 A 3/1997 Ichikawa et al.
5,626,587 A 5/1997 Bishop et al.
5,632,432 A 5/1997 Schulze et al.
5,645,209 A 7/1997 Green et al.
5,647,526 A 7/1997 Green et al.
5,653,374 A 8/1997 Young et al.
5,658,300 A 8/1997 Bito et al.
5,662,662 A 9/1997 Bishop et al.
5,667,517 A 9/1997 Hooven
5,693,042 A 12/1997 Boiarski et al.
5,704,534 A 1/1998 Huitema et al.
5,713,505 A 2/1998 Huitema
5,762,603 A 6/1998 Thompson
5,779,130 A 7/1998 Alesi et al.
5,782,396 A 7/1998 Mastri et al.
5,782,397 A 7/1998 Koukline
5,792,573 A 8/1998 Pitzen et al.
5,797,536 A 8/1998 Smith et al.
5,820,009 A 10/1998 Melling et al.
5,863,159 A 1/1999 Lasko
5,908,427 A 6/1999 McKean et al.
5,954,259 A 9/1999 Viola et al.
5,964,774 A 10/1999 McKean et al.
5,993,454 A 11/1999 Longo
6,010,054 A 1/2000 Johnson et al.
6,017,354 A 1/2000 Culp et al.
6,032,849 A 3/2000 Mastri et al.
6,045,560 A 4/2000 McKean et al.
6,090,123 A 7/2000 Culp et al.
6,126,651 A 10/2000 Mayer
6,129,547 A 10/2000 Cise et al.
6,165,169 A 12/2000 Panescu et al.
6,239,732 B1 5/2001 Cusey
6,241,139 B1 6/2001 Milliman et al.
6,264,086 B1 7/2001 McGuckin, Jr.
6,264,087 B1 7/2001 Whitman
6,302,311 B1 10/2001 Adams et al.
6,315,184 B1 11/2001 Whitman
6,321,855 B1 11/2001 Barnes
6,329,778 B1 12/2001 Culp et al.
6,343,731 B1 2/2002 Adams et al.
6,348,061 B1 2/2002 Whitman
6,368,324 B1 4/2002 Dinger et al.
6,371,909 B1 4/2002 Hoeg et al.
6,434,507 B1 8/2002 Clayton et al.
6,443,973 B1 9/2002 Whitman
6,461,372 B1 10/2002 Jensen et al.
6,488,197 B1 12/2002 Whitman
6,491,201 B1 12/2002 Whitman
6,533,157 B1 3/2003 Whitman
6,537,280 B2 3/2003 Dinger et al.
6,610,066 B2 8/2003 Dinger et al.
6,611,793 B1 8/2003 Burnside et al.
6,645,218 B1 11/2003 Cassidy et al.
6,654,999 B2 12/2003 Stoddard et al.
6,698,643 B2 3/2004 Whitman
6,699,177 B1 3/2004 Wang et al.
6,716,233 B1 4/2004 Whitman
6,743,240 B2 6/2004 Smith et al.
6,783,533 B2 8/2004 Green et al.
6,792,390 B1 9/2004 Burnside et al.
6,793,652 B1 9/2004 Whitman et al.
6,817,508 B1 11/2004 Racenet et al.
6,830,174 B2 12/2004 Hillstead et al.
6,846,308 B2 1/2005 Whitman et al.
6,846,309 B2 1/2005 Whitman et al.
6,849,071 B2 2/2005 Whitman et al.
6,860,892 B1 3/2005 Tanaka et al.
6,899,538 B2 5/2005 Matoba
6,905,057 B2 6/2005 Swayze et al.
6,959,852 B2 11/2005 Shelton, IV et al.
6,964,363 B2 11/2005 Wales et al.
6,981,628 B2 1/2006 Wales
6,981,941 B2 1/2006 Whitman et al.
6,986,451 B1 1/2006 Mastri et al.
6,988,649 B2 1/2006 Shelton, IV et al.
7,032,798 B2 4/2006 Whitman et al.
RE39,152 E 6/2006 Aust et al.
7,055,731 B2 6/2006 Shelton, IV et al.
7,059,508 B2 6/2006 Shelton, IV et al.
7,077,856 B2 7/2006 Whitman
7,111,769 B2 9/2006 Wales et al.
7,122,029 B2 10/2006 Koop et al.
7,140,528 B2 11/2006 Shelton, IV
7,141,049 B2 11/2006 Stern et al.
7,143,923 B2 12/2006 Shelton, IV et al.
7,143,925 B2 12/2006 Shelton, IV et al.
7,143,926 B2 12/2006 Shelton, IV et al.
7,147,138 B2 12/2006 Shelton, IV
7,172,104 B2 2/2007 Scirica et al.
7,225,964 B2 6/2007 Mastri et al.
7,238,021 B1 7/2007 Johnson
7,246,734 B2 7/2007 Shelton, IV
7,252,660 B2 8/2007 Kunz
7,328,828 B2 2/2008 Ortiz et al.
7,364,061 B2 4/2008 Swayze et al.
7,380,695 B2 6/2008 Doll et al.
7,380,696 B2 6/2008 Shelton, IV et al.
7,404,508 B2 7/2008 Smith et al.
7,407,078 B2 8/2008 Shelton, IV et al.
7,416,101 B2 8/2008 Shelton, IV et al.
7,419,080 B2 9/2008 Smith et al.

(56) References Cited

U.S. PATENT DOCUMENTS 7,422,139 B2 9/2008 Shelton, IV et al.
7,431,189 B2 10/2008 Shelton, IV et al.
7,441,684 B2 10/2008 Shelton, IV et al.
7,448,525 B2 11/2008 Shelton, IV et al.
7,464,846 B2 12/2008 Shelton, IV et al.
7,464,847 B2 12/2008 Viola et al.
7,464,849 B2 12/2008 Shelton, IV et al.
7,481,347 B2 1/2009 Roy
7,481,824 B2 1/2009 Boudreaux et al.
7,487,899 B2 2/2009 Shelton, IV et al.
7,549,564 B2 6/2009 Boudreaux
7,565,993 B2 7/2009 Milliman et al.
7,568,603 B2 8/2009 Shelton, IV et al.
7,575,144 B2 8/2009 Ortiz et al.
7,588,175 B2 9/2009 Timm et al.
7,588,176 B2 9/2009 Timm et al.
7,637,409 B2 12/2009 Marczyk
7,641,093 B2 1/2010 Doll et al.
7,644,848 B2 1/2010 Swayze et al.
7,670,334 B2 3/2010 Hueil et al.
7,673,780 B2 3/2010 Shelton, IV et al.
7,699,835 B2 4/2010 Lee et al.
7,721,931 B2 5/2010 Shelton, IV et al.
7,738,971 B2 6/2010 Swayze et al.
7,740,159 B2 6/2010 Shelton, IV et al.
7,743,960 B2 6/2010 Whitman et al.
7,758,613 B2 7/2010 Whitman
7,766,210 B2 8/2010 Shelton, IV et al.
7,770,773 B2 8/2010 Whitman et al.
7,770,775 B2 8/2010 Shelton, IV et al.
7,793,812 B2 9/2010 Moore et al.
7,799,039 B2 9/2010 Shelton, IV et al.
7,802,712 B2 9/2010 Milliman et al.
7,803,151 B2 9/2010 Whitman
7,822,458 B2 10/2010 Webster, III et al.
7,845,534 B2 12/2010 Viola et al.
7,845,537 B2 12/2010 Shelton, IV et al.
7,857,185 B2 12/2010 Swayze et al.
7,870,989 B2 1/2011 Viola et al.
7,900,805 B2 3/2011 Shelton, IV et al.
7,905,897 B2 3/2011 Whitman et al.
7,918,230 B2 4/2011 Whitman et al.
7,922,061 B2 4/2011 Shelton, IV et al.
7,922,719 B2 4/2011 Ralph et al.
7,947,034 B2 5/2011 Whitman
7,951,071 B2 5/2011 Whitman et al.
7,954,682 B2 6/2011 Giordano et al.
7,959,051 B2 6/2011 Smith et al.
7,963,433 B2 6/2011 Whitman et al.
7,967,178 B2 6/2011 Scirica et al.
7,967,179 B2 6/2011 Olson et al.
7,992,758 B2 8/2011 Whitman et al.
8,011,550 B2 9/2011 Aranyi et al.
8,016,178 B2 9/2011 Olson et al.
8,016,855 B2 9/2011 Whitman et al.
8,020,743 B2 9/2011 Shelton, IV
8,025,199 B2 9/2011 Whitman et al.
8,035,487 B2 10/2011 Malackowski
8,052,024 B2 11/2011 Viola et al.
8,114,118 B2 2/2012 Knodel et al.
8,127,975 B2 3/2012 Olson et al.
8,132,705 B2 3/2012 Viola et al.
8,152,516 B2 4/2012 Harvey et al.
8,157,150 B2 4/2012 Viola et al.
8,157,151 B2 4/2012 Ingmanson et al.
8,182,494 B1 5/2012 Yencho et al.
8,186,555 B2 5/2012 Shelton, IV et al.
8,186,587 B2 5/2012 Zmood et al.
8,220,367 B2 7/2012 Hsu
8,235,273 B2 8/2012 Olson et al.
8,241,322 B2 8/2012 Whitman et al.
8,272,554 B2 9/2012 Whitman et al.
8,292,150 B2 10/2012 Bryant
8,292,888 B2 10/2012 Whitman
8,342,379 B2 1/2013 Whitman et al.
8,348,130 B2 1/2013 Shah et al.
8,348,855 B2 1/2013 Hillely et al.
8,353,440 B2 1/2013 Whitman et al.
8,357,144 B2 1/2013 Whitman et al.
8,365,633 B2 2/2013 Simaan et al.
8,365,972 B2 2/2013 Aranyi et al.
8,371,492 B2 2/2013 Aranyi et al.
8,372,057 B2 2/2013 Cude et al.
8,391,957 B2 3/2013 Carlson et al.
8,403,926 B2 3/2013 Nobis et al.
8,418,904 B2 4/2013 Wenchell et al.
8,424,739 B2 4/2013 Racenet et al.
8,454,585 B2 6/2013 Whitman
8,505,802 B2 8/2013 Viola et al.
8,517,241 B2 8/2013 Nicholas et al.
8,523,043 B2 9/2013 Ullrich et al.
8,551,076 B2 10/2013 Duval et al.
8,561,871 B2 10/2013 Rajappa et al.
8,561,874 B2 10/2013 Scirica
8,602,287 B2 12/2013 Yates et al.
8,623,000 B2 1/2014 Humayun et al.
8,627,995 B2 1/2014 Smith et al.
8,632,463 B2 1/2014 Drinan et al.
8,636,766 B2 1/2014 Milliman et al.
8,647,258 B2 2/2014 Aranyi et al.
8,652,121 B2 2/2014 Quick et al.
8,657,174 B2 2/2014 Yates et al.
8,657,177 B2 2/2014 Scirica et al.
8,672,206 B2 3/2014 Aranyi et al.
8,696,552 B2 4/2014 Whitman
8,708,213 B2 4/2014 Shelton, IV et al.
8,715,306 B2 5/2014 Faller et al.
8,758,391 B2 6/2014 Swayze et al.
8,806,973 B2 8/2014 Ross et al.
8,808,311 B2 8/2014 Heinrich et al.
8,820,605 B2 9/2014 Shelton, IV
8,851,355 B2 10/2014 Aranyi et al.
8,858,571 B2 10/2014 Shelton, IV et al.
8,875,972 B2 11/2014 Weisenburgh, II et al.
8,888,762 B2 11/2014 Whitman
8,893,946 B2 11/2014 Boudreaux et al.
8,899,462 B2 12/2014 Kostrzewski et al.
8,905,289 B2 12/2014 Patel et al.
8,919,630 B2 12/2014 Milliman
8,931,680 B2 1/2015 Milliman
8,939,344 B2 1/2015 Olson et al.
8,950,646 B2 2/2015 Viola
8,960,519 B2 2/2015 Whitman et al.
8,961,396 B2 2/2015 Azarbarzin et al.
8,967,443 B2 3/2015 McCuen
8,968,276 B2 3/2015 Zemlok et al.
8,968,337 B2 3/2015 Whitfield et al.
8,992,422 B2 3/2015 Spivey et al.
9,016,545 B2 4/2015 Aranyi et al.
9,023,014 B2 5/2015 Chowaniec et al.
9,033,868 B2 5/2015 Whitman et al.
9,055,943 B2 6/2015 Zemlok et al.
9,064,653 B2 6/2015 Prest et al.
9,072,515 B2 7/2015 Hall et al.
9,113,847 B2 8/2015 Whitman et al.
9,113,875 B2 8/2015 Viola et al.
9,113,876 B2 8/2015 Zemlok et al.
9,113,899 B2 8/2015 Garrison et al.
9,216,013 B2 12/2015 Scirica et al.
9,241,712 B2 1/2016 Zemlok et al.
9,282,961 B2 3/2016 Whitman et al.
9,282,963 B2 3/2016 Bryant
9,295,522 B2 3/2016 Kostrzewski
9,307,986 B2 4/2016 Hall et al.
9,763,661 B2 9/2017 Zergiebel et al.
10,080,552 B2 9/2018 Nicholas et al.
10,111,665 B2 10/2018 Aranyi
10,253,847 B2 4/2019 Nicholas
2001/0031975 A1 10/2001 Whitman et al.
2002/0049454 A1 4/2002 Whitman et al.
2002/0165541 A1 11/2002 Whitman
2003/0038938 A1 2/2003 Jung et al.
2003/0165794 A1 9/2003 Matoba
2004/0034369 A1 2/2004 Sauer et al.

(56) References Cited

U.S. PATENT DOCUMENTS

| | | | |
|---|---|---|---|
| 2004/0111012 | A1 | 6/2004 | Whitman |
| 2004/0133189 | A1 | 7/2004 | Sakurai |
| 2004/0153124 | A1 | 8/2004 | Whitman |
| 2004/0176751 | A1 | 9/2004 | Weitzner et al. |
| 2004/0193146 | A1 | 9/2004 | Lee et al. |
| 2005/0125027 | A1 | 6/2005 | Knodel et al. |
| 2005/0131442 | A1 | 6/2005 | Yachia et al. |
| 2006/0142656 | A1 | 6/2006 | Malackowski et al. |
| 2006/0142740 | A1 | 6/2006 | Sherman et al. |
| 2006/0142744 | A1 | 6/2006 | Boutoussov |
| 2006/0259073 | A1 | 11/2006 | Miyamoto et al. |
| 2006/0278680 | A1 | 12/2006 | Viola et al. |
| 2006/0284730 | A1 | 12/2006 | Schmid et al. |
| 2007/0023476 | A1 | 2/2007 | Whitman et al. |
| 2007/0023477 | A1 | 2/2007 | Whitman et al. |
| 2007/0027469 | A1 | 2/2007 | Smith et al. |
| 2007/0029363 | A1 | 2/2007 | Popov |
| 2007/0084897 | A1 | 4/2007 | Shelton et al. |
| 2007/0102472 | A1 | 5/2007 | Shelton |
| 2007/0152014 | A1 | 7/2007 | Gillum et al. |
| 2007/0175947 | A1 | 8/2007 | Ortiz et al. |
| 2007/0175949 | A1 | 8/2007 | Shelton et al. |
| 2007/0175950 | A1 | 8/2007 | Shelton et al. |
| 2007/0175951 | A1 | 8/2007 | Shelton et al. |
| 2007/0175955 | A1 | 8/2007 | Shelton et al. |
| 2007/0175961 | A1 | 8/2007 | Shelton et al. |
| 2007/0270784 | A1 | 11/2007 | Smith et al. |
| 2008/0029570 | A1 | 2/2008 | Shelton et al. |
| 2008/0029573 | A1 | 2/2008 | Shelton et al. |
| 2008/0029574 | A1 | 2/2008 | Shelton et al. |
| 2008/0029575 | A1 | 2/2008 | Shelton et al. |
| 2008/0058801 | A1 | 3/2008 | Taylor et al. |
| 2008/0109012 | A1 | 5/2008 | Falco et al. |
| 2008/0110958 | A1 | 5/2008 | McKenna et al. |
| 2008/0147089 | A1 | 6/2008 | Loh et al. |
| 2008/0167736 | A1 | 7/2008 | Swayze et al. |
| 2008/0185419 | A1 | 8/2008 | Smith et al. |
| 2008/0188841 | A1 | 8/2008 | Tomasello et al. |
| 2008/0197167 | A1 | 8/2008 | Viola et al. |
| 2008/0208195 | A1 | 8/2008 | Shores et al. |
| 2008/0237296 | A1 | 10/2008 | Boudreaux et al. |
| 2008/0251561 | A1 | 10/2008 | Eades et al. |
| 2008/0255413 | A1 | 10/2008 | Zemlok et al. |
| 2008/0255607 | A1 | 10/2008 | Zemlok |
| 2008/0262654 | A1 | 10/2008 | Omori et al. |
| 2008/0308603 | A1 | 12/2008 | Shelton et al. |
| 2009/0012533 | A1 | 1/2009 | Barbagli et al. |
| 2009/0090763 | A1 | 4/2009 | Zemlok et al. |
| 2009/0099876 | A1 | 4/2009 | Whitman |
| 2009/0138006 | A1 | 5/2009 | Bales et al. |
| 2009/0171147 | A1 | 7/2009 | Lee et al. |
| 2009/0182193 | A1 | 7/2009 | Whitman et al. |
| 2009/0209946 | A1 | 8/2009 | Swayze |
| 2009/0209990 | A1 | 8/2009 | Yates et al. |
| 2009/0254094 | A1 | 10/2009 | Knapp et al. |
| 2009/0299141 | A1 | 12/2009 | Downey et al. |
| 2010/0023022 | A1 | 1/2010 | Zeiner et al. |
| 2010/0069942 | A1 | 3/2010 | Shelton, IV |
| 2010/0193568 | A1 | 8/2010 | Scheib et al. |
| 2010/0211053 | A1 | 8/2010 | Ross et al. |
| 2010/0225073 | A1 | 9/2010 | Porter et al. |
| 2011/0071508 | A1 | 3/2011 | Duval et al. |
| 2011/0077673 | A1 | 3/2011 | Grubac et al. |
| 2011/0121049 | A1 | 5/2011 | Malinouskas et al. |
| 2011/0125138 | A1 | 5/2011 | Malinouskas et al. |
| 2011/0139851 | A1 | 6/2011 | McCuen |
| 2011/0155783 | A1 | 6/2011 | Rajappa et al. |
| 2011/0155786 | A1 | 6/2011 | Shelton, IV |
| 2011/0172648 | A1 | 7/2011 | Jeong |
| 2011/0174009 | A1 | 7/2011 | Iizuka et al. |
| 2011/0174099 | A1 | 7/2011 | Ross et al. |
| 2011/0184245 | A1 | 7/2011 | Xia et al. |
| 2011/0204119 | A1 | 8/2011 | McCuen |
| 2011/0218522 | A1 | 9/2011 | Whitman |
| 2011/0276057 | A1 | 11/2011 | Conlon et al. |
| 2011/0290854 | A1 | 12/2011 | Timm et al. |
| 2011/0295242 | A1 | 12/2011 | Spivey et al. |
| 2011/0295269 | A1 | 12/2011 | Swensgard et al. |
| 2011/0295270 | A1 | 12/2011 | Giordano et al. |
| 2012/0000962 | A1 | 1/2012 | Racenet et al. |
| 2012/0074199 | A1 | 3/2012 | Olson et al. |
| 2012/0089131 | A1 | 4/2012 | Zemlok et al. |
| 2012/0104071 | A1 | 5/2012 | Bryant |
| 2012/0116368 | A1 | 5/2012 | Viola |
| 2012/0143002 | A1 | 6/2012 | Aranyi et al. |
| 2012/0172924 | A1 | 7/2012 | Allen, IV |
| 2012/0211542 | A1 | 8/2012 | Racenet |
| 2012/0223121 | A1 | 9/2012 | Viola et al. |
| 2012/0245428 | A1 | 9/2012 | Smith et al. |
| 2012/0253329 | A1 | 10/2012 | Zemlok et al. |
| 2012/0310220 | A1 | 12/2012 | Malkowski et al. |
| 2012/0323226 | A1 | 12/2012 | Chowaniec et al. |
| 2012/0330285 | A1 | 12/2012 | Hartoumbekis et al. |
| 2013/0093149 | A1 | 4/2013 | Saur et al. |
| 2013/0181035 | A1 | 7/2013 | Milliman |
| 2013/0184704 | A1 | 7/2013 | Beardsley et al. |
| 2013/0214025 | A1 | 8/2013 | Zemlok et al. |
| 2013/0274722 | A1 | 10/2013 | Kostrzewski et al. |
| 2013/0282052 | A1 | 10/2013 | Aranyi et al. |
| 2013/0292451 | A1 | 11/2013 | Viola et al. |
| 2013/0313304 | A1 | 11/2013 | Shelton, IV et al. |
| 2013/0317486 | A1 | 11/2013 | Nicholas et al. |
| 2013/0319706 | A1 | 12/2013 | Nicholas et al. |
| 2013/0324978 | A1 | 12/2013 | Nicholas et al. |
| 2013/0324979 | A1 | 12/2013 | Nicholas et al. |
| 2013/0334281 | A1 | 12/2013 | Williams |
| 2014/0012236 | A1 | 1/2014 | Williams et al. |
| 2014/0012237 | A1 | 1/2014 | Pribanic et al. |
| 2014/0012289 | A1 | 1/2014 | Snow et al. |
| 2014/0025046 | A1 | 1/2014 | Williams et al. |
| 2014/0110455 | A1 | 4/2014 | Ingmanson et al. |
| 2014/0166717 | A1 | 6/2014 | Swayze et al. |
| 2014/0207125 | A1 | 7/2014 | Applegate et al. |
| 2014/0207182 | A1 | 7/2014 | Zergiebel et al. |
| 2014/0207185 | A1 | 7/2014 | Goble et al. |
| 2014/0236174 | A1 | 8/2014 | Williams et al. |
| 2014/0276932 | A1 | 9/2014 | Williams et al. |
| 2014/0299647 | A1 | 10/2014 | Scirica et al. |
| 2014/0303668 | A1 | 10/2014 | Nicholas et al. |
| 2014/0358129 | A1 | 12/2014 | Zergiebel et al. |
| 2014/0361068 | A1 | 12/2014 | Aranyi et al. |
| 2014/0365235 | A1 | 12/2014 | DeBoer et al. |
| 2014/0373652 | A1 | 12/2014 | Zergiebel et al. |
| 2015/0014392 | A1 | 1/2015 | Williams et al. |
| 2015/0048144 | A1 | 2/2015 | Whitman |
| 2015/0076205 | A1 | 3/2015 | Zergiebel |
| 2015/0080912 | A1 | 3/2015 | Sapre |
| 2015/0112381 | A1 | 4/2015 | Richard |
| 2015/0122870 | A1 | 5/2015 | Zemlok et al. |
| 2015/0133224 | A1 | 5/2015 | Whitman et al. |
| 2015/0150547 | A1 | 6/2015 | Ingmanson et al. |
| 2015/0150574 | A1 | 6/2015 | Richard et al. |
| 2015/0157320 | A1 | 6/2015 | Zergiebel et al. |
| 2015/0157321 | A1 | 6/2015 | Zergiebel et al. |
| 2015/0164502 | A1 | 6/2015 | Richard et al. |
| 2015/0201931 | A1 | 7/2015 | Zergiebel et al. |
| 2015/0272577 | A1 | 10/2015 | Zemlok et al. |
| 2015/0297199 | A1 | 10/2015 | Nicholas et al. |
| 2015/0303996 | A1 | 10/2015 | Calderoni |
| 2015/0320420 | A1 | 11/2015 | Penna et al. |
| 2015/0327850 | A1 | 11/2015 | Kostrzewski |
| 2015/0342601 | A1 | 12/2015 | Williams et al. |
| 2015/0342603 | A1 | 12/2015 | Zergiebel et al. |
| 2015/0374366 | A1 | 12/2015 | Zergiebel et al. |
| 2015/0374370 | A1 | 12/2015 | Zergiebel et al. |
| 2015/0374371 | A1 | 12/2015 | Richard et al. |
| 2015/0374372 | A1 | 12/2015 | Zergiebel et al. |
| 2015/0374449 | A1 | 12/2015 | Chowaniec et al. |
| 2015/0380187 | A1 | 12/2015 | Zergiebel et al. |
| 2016/0095585 | A1 | 4/2016 | Zergiebel et al. |
| 2016/0095596 | A1 | 4/2016 | Scirica et al. |
| 2016/0100839 | A1* | 4/2016 | Marczyk ................ A61B 90/98<br>227/175.3 |

(56) References Cited

U.S. PATENT DOCUMENTS

| | | | | |
|---|---|---|---|---|
| 2016/0106406 A1* | 4/2016 | Cabrera | A61B 17/1155 606/1 |
| 2016/0113648 A1 | 4/2016 | Zergiebel et al. | |
| 2016/0113649 A1* | 4/2016 | Zergiebel | A61B 90/03 227/175.2 |
| 2016/0118201 A1 | 4/2016 | Nicholas et al. | |
| 2016/0249909 A1* | 9/2016 | Shelton, IV | A61L 2/28 227/176.1 |
| 2016/0310134 A1 | 10/2016 | Contini et al. | |
| 2016/0324518 A1 | 11/2016 | Nicholas et al. | |

FOREIGN PATENT DOCUMENTS

| | | | |
|---|---|---|---|
| CN | 1957854 | A | 5/2007 |
| CN | 101495046 | A | 7/2009 |
| CN | 102247182 | A | 11/2011 |
| DE | 102008053842 | A1 | 5/2010 |
| EP | 0705571 | A1 | 4/1996 |
| EP | 1563793 | A1 | 8/2005 |
| EP | 1769754 | A1 | 4/2007 |
| EP | 1813211 | A2 | 8/2007 |
| EP | 1982657 | A2 | 10/2008 |
| EP | 2055243 | A2 | 5/2009 |
| EP | 2316345 | A1 | 5/2011 |
| EP | 2668910 | A2 | 12/2013 |
| EP | 2792308 | A2 | 10/2014 |
| ES | 2333509 | A1 | 2/2010 |
| JP | 2005125075 | A | 5/2005 |
| KR | 20120022521 | A | 3/2012 |
| WO | 2009039506 | A1 | 3/2009 |
| WO | 2011108840 | A2 | 9/2011 |
| WO | 2012040984 | A1 | 4/2012 |
| WO | 2014172208 | A1 | 10/2014 |

OTHER PUBLICATIONS

Canadian Office Action corresponding to counterpart International Application No. CA 2640399 dated May 7, 2015.

Japanese Office Action corresponding to counterpart International Application No. JP 2011-197365 dated Mar. 23, 2015.

Japanese Office Action corresponding to counterpart International Application No. JP 2011-084092 dated May 20, 2015.

Japanese Office Action corresponding to counterpart International Application No. JP 2014-148482 dated Jun. 2, 2015.

Extended European Search Report corresponding to counterpart International Application No. EP 14 18 9358.6 dated Jul. 8, 2015.

Extended European Search Report corresponding to counterpart International Application No. EP 14 19 6148.2 dated Apr. 23, 2015.

Partial European Search Report corresponding to counterpart International Application No. EP 14 19 6704.2 dated May 11, 2015.

Australian Office Action corresponding to counterpart International Application No. AU 2010241367 dated Aug. 20, 2015.

Partial European Search Report corresponding to counterpart International Application No. EP 14 19 97833 dated Sep. 3, 2015.

Extended European Search Report corresponding to counterpart International Application No. EP 15 16 9962.6 dated Sep. 14, 2015.

Extended European Search Report corresponding to International Application No. EP 15 15 1076.5 dated Apr. 22, 2015.

Japanese Office Action corresponding to International Application No. JP 2011-084092 dated Jan. 14, 2016.

Extended European Search Report corresponding to International Application No. EP 12 19 7970.2 dated Jan. 28, 2016.

Chinese Office Action corresponding to International Application No. CN 201210560638.1 dated Oct. 21, 2015.

European Office Action corresponding to International Application No. EP 14 15 9056.2 dated Oct. 26, 2015.

Australian Examination Report No. 1 corresponding to International Application No. AU 2015200153 dated Dec. 11, 2015.

Australian Examination Report No. 1 corresponding to International Application No. AU 2014204542 dated Jan. 7, 2016.

Chinese Office Action corresponding to International Application No. CN 201310125449.6 dated Feb. 3, 2016.

Extended European Search Report corresponding to International Application No. EP 15 19 0245.9 dated Jan. 28, 2016.

Extended European Search Report corresponding to International Application No. EP 15 16 7793.7 dated Apr. 5, 2016.

European Office Action corresponding to International Application No. EP 14 18 4882.0 dated Apr. 25, 2016.

Extended European Search Report corresponding to International Application No. EP 14 19 6704.2 dated Sep. 24, 2015.

International Search Report and Written Opinion corresponding to Int'l Appln. No. PCT/US2015/051837, dated Dec. 21, 2015.

Extended European Search Report corresponding to International Application No. EP 14 19 7563.1 dated Aug. 5, 2015.

Partial European Search Report corresponding to International Application No. EP 15 19 0643.5 dated Feb. 26, 2016.

Extended European Search Report corresponding to International Application No. EP 15 16 6899.3 dated Feb. 3, 2016.

Extended European Search Report corresponding to International Application No. EP 14 19 9783.3 dated Dec. 22, 2015.

Extended European Search Report corresponding to International Application No. EP 15 17 3807.7 dated Nov. 24, 2015.

Extended European Search Report corresponding to International Application No. EP 15 19 0760.7 dated Apr. 1, 2016.

Extended European Search Report corresponding to International Application No. EP 15 17 3803.6 dated Nov. 24, 2015.

Extended European Search Report corresponding to International Application No. EP 15 17 3804.4 dated Nov. 24, 2015.

Extended European Search Report corresponding to International Application No. EP 15 18 8539.9 dated Feb. 17, 2016.

Extended European Search Report corresponding to International Application No. EP 15 17 3910.9 dated Nov. 13, 2015.

European Office Action corresponding to International Application No. EP 14 15 2236.7 dated Aug. 11, 2015.

Extended European Search Report corresponding to International Application No. EP 15 18 4915.5 dated Jan. 5, 2016.

Chinese Office Action corresponding to counterpart Int'l, Appin. No. CN 201310369318.2 dated Jun. 28, 2016.

Chinese Office Action (with English translation), dated Jul. 4, 2016, corresponding to Chinese Patent Application No. 2015101559718; 23 total pages.

European Search Report EP 15 156 035.6 dated Aug. 10, 2016.

Australian Examination Report No. 1 corresponding to International Application No. AU 2013205872 dated Oct. 19, 2016.

Australian Examination Report from Appl. No. AU 2013205840 dated Nov. 3, 2016.

European Search Report corresponding to EP 15 184 915.5-1654 dated Sep. 16, 2016.

Extended European Search Report issused in EP 16205717 dated May 15, 2017.

Japanese Office Action for application No. 2016-249260 dated Nov. 6, 2020 with English translation.

* cited by examiner 200c
200
200e
200g
302
200
302

ELECTROMECHANICAL SURGICAL DEVICES WITH SINGLE MOTOR DRIVES AND ADAPTER ASSEMBLIES THERFOR

CROSS-REFERENCE TO RELATED APPLICATIONS

This application is a continuation of U.S. patent application Ser. No. 15/368,869, filed Dec. 5, 2016, which claims the benefit of U.S. Provisional Patent Application Ser. No. 62/270,804, filed Dec. 22, 2015, the entire disclosure of each of which are incorporated by reference herein.

TECHNICAL FIELD

The present disclosure relates to surgical systems, and more specifically, to surgical systems having electromechanical surgical devices, including hand-held electromechanical surgical devices, with single motor drives and adapter assemblies for interconnecting the electromechanical surgical devices to end effectors or surgical loading units.

BACKGROUND

A number of surgical device manufacturers have developed product lines with proprietary powered drive systems for operating and/or manipulating the surgical device. In many instances, the surgical devices include a powered handle assembly, which may be reusable, and an end effector and/or loading unit that is selectively connected to the powered handle assembly prior to use. The powered handle assembly may be disconnected from the loading unit and/or end effector following use so that the end effector, loading unit and/or handle assembly may be disposed of, or in some instances, sterilized for re-use.

Many of the existing end effectors for use with many of the existing powered surgical devices and/or handle assemblies are driven by a linear force. For examples, end effectors or loading units for performing endo-gastrointestinal anastomosis procedures, end-to-end anastomosis procedures and transverse anastomosis procedures, each typically require a linear driving force in order to be operated. Thus, these end effectors or loading units are not compatible with surgical devices and/or handle assemblies that use a rotary motion to deliver power or the like.

In order to make the linear driven end effectors or loading units compatible with powered surgical devices and/or handle assemblies that use a rotary motion to deliver power, adapter assemblies are used to interface between and interconnect the linear driven end effectors with the powered rotary driven surgical devices and/or handle assemblies. Many of these surgical devices and/or adapter assemblies are complex devices including many parts and requiring extensive labor to assemble.

Accordingly, a need exists to develop surgical devices and/or adapter assemblies that incorporate fewer parts, are less labor intensive to assemble, and are ultimately more economical to manufacture and use.

SUMMARY

The present disclosure relates to surgical systems, and more specifically, to surgical systems having electromechanical surgical devices, including hand-held electromechanical surgical devices, with single motor drives and adapter assemblies for interconnecting the electromechanical surgical devices to end effectors or loading units. The electromechanical surgical devices include handle assemblies supporting selector motors that coordinate engagement of output assemblies and the single motor drives. The output assemblies engage input couplers supported by the adapter assemblies. The input couplers can be operatively coupled to the end effectors or loading units so that rotation forces from the output assemblies enable the end effectors or loading units to perform one or more functions.

According to an aspect of the present disclosure, an electromechanical surgical system includes a handle assembly, a drive motor, a selector cam, a selector motor, a first output assembly, and a second output assembly.

The drive motor may be supported in the handle assembly and may extend to a drive gear.

The selector cam may define a recess. The selector cam may include a compression surface adjacent to the recess of the selector cam. In some embodiments, the recess includes tapered sidewalls.

The selector motor may extend to a selector gear. The selector gear may be positioned to move the selector cam between a first position and a second position.

The first output assembly includes a first output shaft and a first output gear. The first output shaft is selectively coupled to the first output gear by a first engagement key. The first output gear is rotatable with the drive gear of the drive motor. The first engagement key is positionable within the recess of the selector cam while the selector cam is in the first position to engage the first output gear with the first output shaft. The first output shaft is rotatable with the first output gear in response to rotation of the drive gear of the drive motor while the first output gear is coupled to the first output shaft. The first output gear is rotatable relative to the first output shaft while the selector cam is in the second position.

The second output assembly includes a second output shaft and a second output gear. The second output shaft is selectively coupled to the second output gear by a second engagement key. The second output gear is engaged with the first output gear of the first output assembly. The second engagement key is positionable within the recess of the selector cam while the selector cam is in the second position to engage the second output gear with the second output shaft. The second output shaft is rotatable with the second output gear in response to rotation of the drive gear of the drive motor while the second output gear is coupled to the second output shaft. The second output gear is rotatable relative to the second output shaft while the selector cam is in the first position.

In some embodiments, the first engagement key and the first output shaft may be coupled by a first spring. The first spring may be positioned to bias the first engagement key toward the selector cam. The compression surface of the selector cam may be positioned to urge the first engagement key toward the first output shaft and exert compression forces on the first spring while the first engagement key is in contact with the compression surface of the selector cam.

In certain embodiments, the first engagement key may include a flange extending therefrom and the first output gear may include inner teeth. The flange of the first engagement key may be slidable through a slot defined in the first output shaft between a disengaged position and an engaged position to selectively engage the first output gear with the first output shaft. In the engaged position, the flange of the first engagement key may be engaged with the inner teeth of the first output gear and the slot of the first output shaft so that the first output shaft rotates with the first output shaft. In the disengaged position, the flange of the first engagement key may be engaged with the slot of the first output shaft and spaced from the first output gear such that the first output gear rotates relative to the first output shaft.

The first engagement key may include a rounded tip configured to cam along the tapered sidewalls of the recess of the selector cam as the selector cam moves between the first and second positions.

In certain embodiments, the second engagement key and the second output shaft may be coupled by a second spring positioned to bias the second engagement key toward the selector cam. The compression surface of the selector cam may be positioned to urge the second engagement key toward the second output shaft and exert compression forces on the second spring while the second engagement key is in contact with the compression surface of the selector cam.

In some embodiments, the second engagement key may include a flange extending therefrom and the second output gear may include inner teeth. The flange of the second engagement key may be slidable through a slot defined in the second output shaft between a disengaged position and an engaged position to selectively engage the second output gear with the second output shaft. In the engaged position, the flange of the second engagement key may be engaged with the inner teeth of the second output gear and the slot of the second output shaft so that the second output shaft rotates with the second output shaft. In the disengaged position, the flange of the second engagement key may be engaged with the slot of the second output shaft and spaced from the second output gear such that the second output gear rotates relative to the second output shaft.

In certain embodiments, the second engagement key includes a rounded tip configured to cam along the tapered sidewalls of the recess of the selector cam as the selector cam moves between the first and second positions.

The electromechanical surgical system may include a third output assembly including a third output shaft and a third output gear. The third output shaft may be selectively coupled to the third output gear by a third engagement key. The third output gear may be engaged with the first output gear of the first output assembly. The third engagement key may be positionable within the recess of the selector cam while the selector cam is in a third position to engage the third output gear with the third output shaft. The third output shaft may be rotatable with the third output gear in response to rotation of the drive gear of the drive motor while the third output gear is engaged with the third output shaft. The third output gear may be rotatable relative to the third output shaft while the selector cam in is in the first and second positions.

In some embodiments, the third engagement key and the third output shaft may be coupled by a third spring. The third spring may be positioned to bias the third engagement key toward the selector cam.

The compression surface of the selector cam may be positioned to urge the third engagement key toward the third output shaft and exert compression forces on the third spring while the third engagement key is in contact with the compression surface of the selector cam.

In certain embodiments, the third engagement key may include a flange extending therefrom and the third output gear may include inner teeth. The flange of the third engagement key may be slidable through a slot defined in the third output shaft between a disengaged position and an engaged position to selectively engage the third output gear with the third output shaft. In the engaged position, the flange of the third engagement key may be engaged with the inner teeth of the third output gear and the slot of the third output shaft such that the third output gear and the third output shaft move together. In the disengaged position, the flange of the third engagement key may be engaged with the slot of the third output shaft and spaced from the third output gear so that the third output gear rotates relative to the third output shaft.

According to another aspect of the present disclosure, an electromechanical surgical system includes an adapter assembly having proximal and distal ends, an end effector removably coupled to the distal end of the adapter assembly, and a handle assembly coupled to the proximal end of the adapter assembly. The adapter assembly may be removably coupled to the handle assembly by one or both of: a spring loaded button or a spring loaded ejector pin.

The handle assembly includes a drive motor, a drive gear coupled to the drive motor, a selector cam defining a recess, and a selector motor extending to a selector gear. The selector gear may be positioned to move the selector cam between a first position and a second position. The handle assembly further includes a first output assembly and a second output assembly.

The first output assembly includes a first output shaft and a first output gear. The first output gear may be rotatable with the drive gear of the drive motor. The first output shaft may be rotatable with the first output gear while the selector cam is in the first position.

The second output assembly includes a second output shaft and a second output gear. The second output gear may be engaged with the first output gear of the first output assembly. The second output shaft may be rotatable with the second output gear while the selector cam is in the second position.

In some embodiments, one or both of the first and second output shafts is selectively coupled to a respective one of the first and second output gears by an engagement key.

According to yet another aspect of the present disclosure, an electromechanical surgical system includes an adapter assembly, an end effector, and a handle assembly.

The adapter assembly has proximal and distal ends. The proximal end of the adapter assembly may include first and second input couplers. The loading unit may be removably coupled to the distal end of the adapter assembly and operably coupled to the first and second input couplers of the adapter assembly. The handle assembly is coupled to the proximal end of the adapter assembly.

In some embodiments, the handle assembly includes a drive motor, a drive gear coupled to the drive motor, a selector cam defining a recess, and a selector motor extending to a selector gear. The selector gear may be positioned to move the selector cam between a first position and a second position. The handle assembly may include a first output gear rotatable with the drive gear of the drive motor, a first output shaft rotatable with the first output gear and coupled to the first input coupler of the adapter assembly to drive the first input coupler while the selector cam is in the first position, a second output gear engaged with the first output gear, and a second output shaft rotatable with the second output gear and coupled to the second input coupler of the adapter assembly to drive the second input coupler while the selector cam is in the second position.

Further details and aspects of exemplary embodiments of the present disclosure are described in more detail below with reference to the appended figures.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the disclosure given below, serve to explain the principles of the disclosure, wherein.

DETAILED DESCRIPTION

Figure 1:
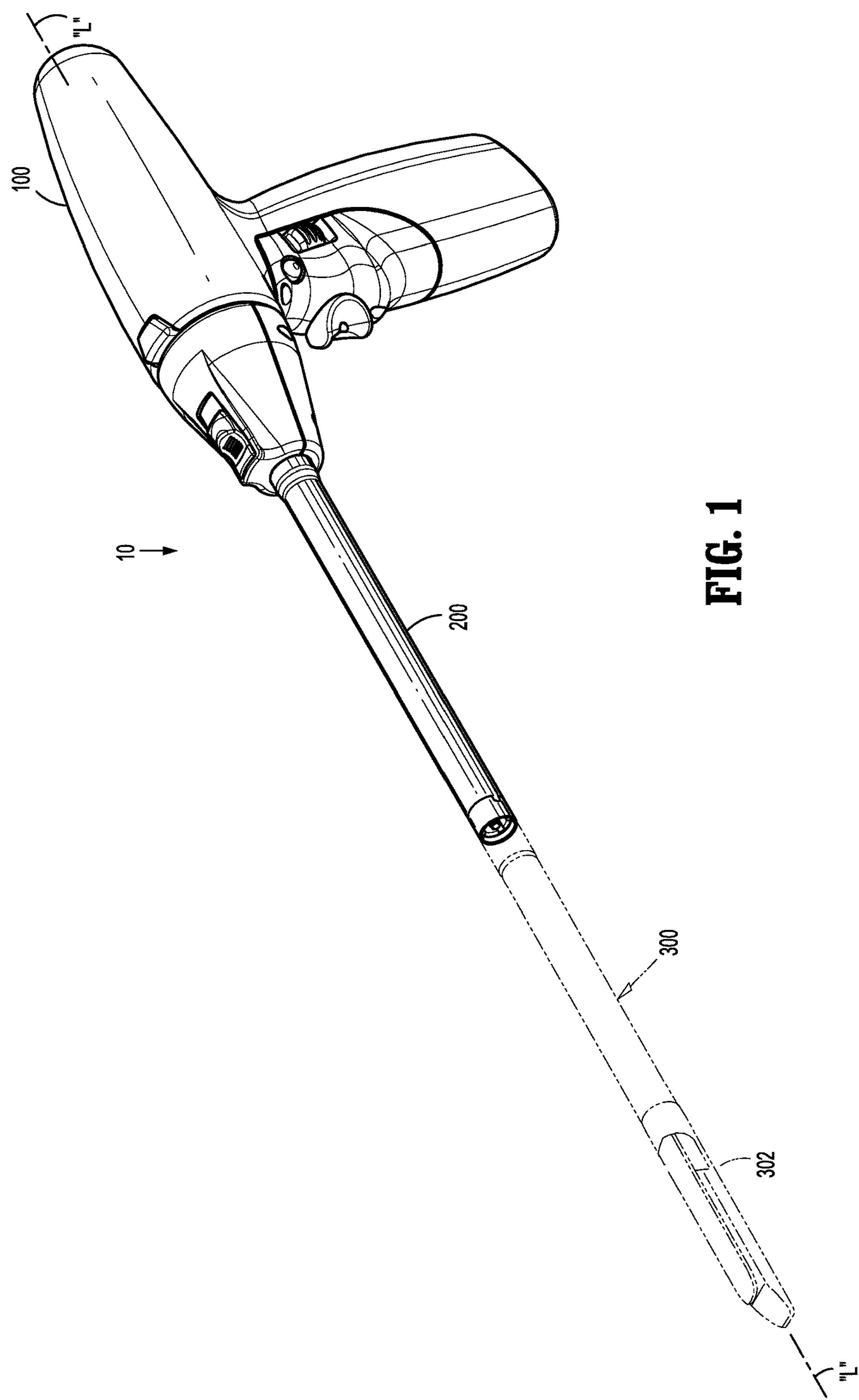
FIG. 1 is a perspective view of an electromechanical surgical system in accordance with the principles of the present disclosure with an exemplary loading unit shown connected thereto in phantom for clarity.

Electromechanical surgical systems of the present disclosure include surgical devices in the form of powered hand-held electromechanical instruments configured for selective attachment to a plurality of different end effectors that are each configured for actuation and manipulation by the powered hand-held electromechanical surgical instrument. In particular, the presently described electromechanical surgical systems include adapter assemblies that interconnect the powered hand-held electromechanical surgical instruments to the plurality of different end effectors for effectuating actuation and/or manipulation thereof.

Embodiments of the presently disclosed electromechanical surgical systems, surgical devices/handle assemblies, adapter assemblies, and/or end effectors/loading units are described in detail with reference to the drawings, in which like reference numerals designate identical or corresponding elements in each of the several views. As used herein, the term "distal" or "leading" refers to that portion of the system, assembly, device, and/or component thereof, farther from the user, while the term "proximal" or "trailing" refers to that portion of the system, assembly, device, and/or component thereof, closer to the user. As used herein, the term "clinician" refers to a doctor, nurse, or other care provider and may include support personnel. As used herein, the term "subject" refers to a human patient or other animal.

Figure 2:
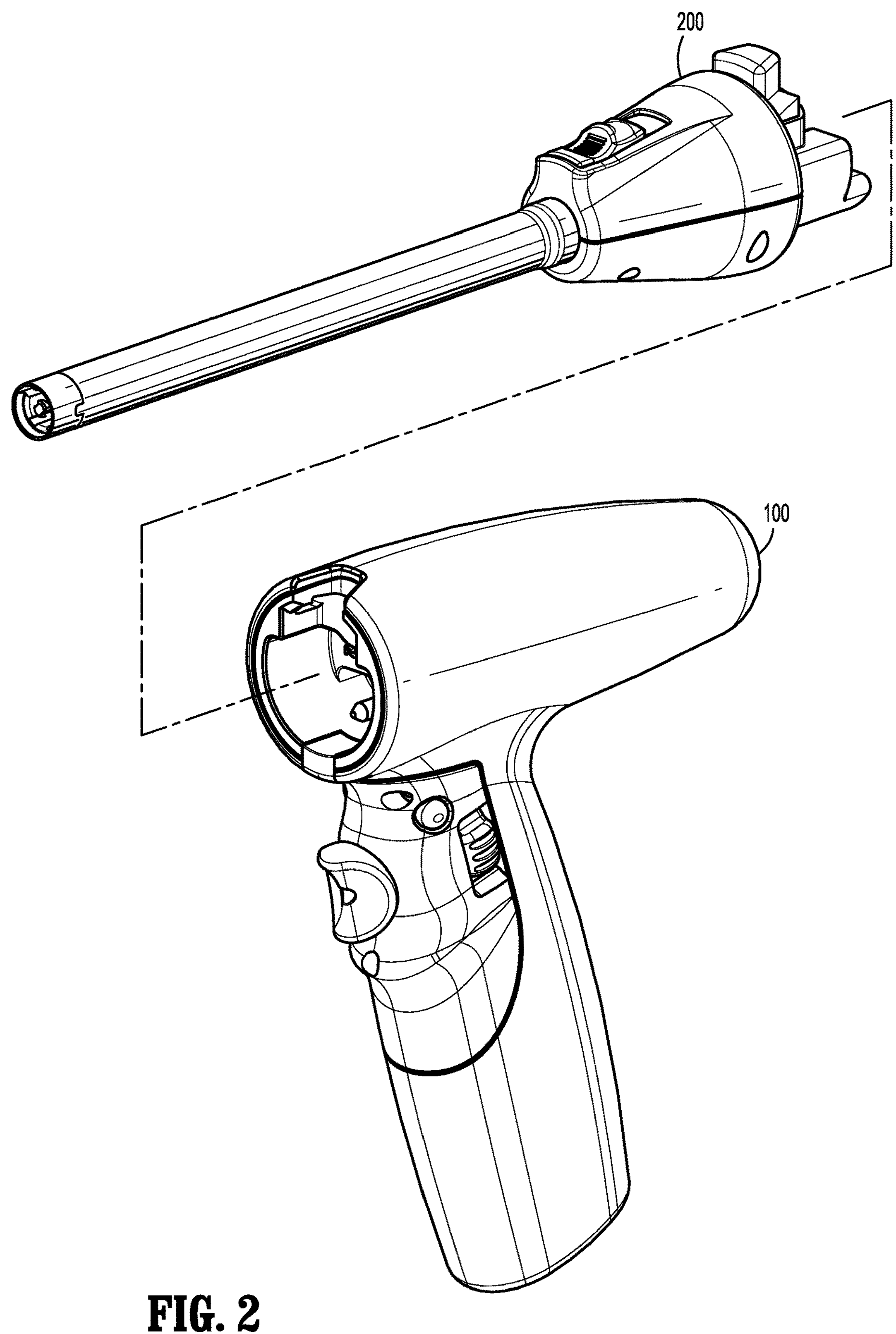
FIG. 2 is a perspective view, with parts separated, of the electromechanical surgical system of FIG. 1.

Turning now to FIGS. 1 and 2, an electromechanical surgical system in accordance with the present disclosure, generally referred to as 10, includes a surgical device or handle assembly 100 in the form of a powered hand-held electromechanical instrument and an adapter assembly 200. Handle assembly 100 is configured for selective connection with adapter assembly 200 and adapter assembly 200 is configured for removable connection to a loading unit 300 (e.g., multiple- or single-use loading unit) including an end effector 302 and/or directly to end effector 302. Together, handle assembly 100 and adapter assembly 200 may cooperate to actuate loading unit 300 and/or end effector 302. Handle assembly 100, adapter assembly 200, and loading unit 300 (and/or end effector 302) define a longitudinal axis "L" therethrough.

In the interest of brevity, although loading unit 300 (and/or end effector 302) is described herein as including surgical stapling components, the loading unit 300 (and/or end effector 302) of the present disclosure may include, or be adapted to include, any type of surgical components. For example, loading unit 300 (and/or end effector 302), or components thereof, may include, but is/are not limited to, one or more components of a surgical stapler, a surgical clip applier, a surgical grasping device, etc.

Figure 3:
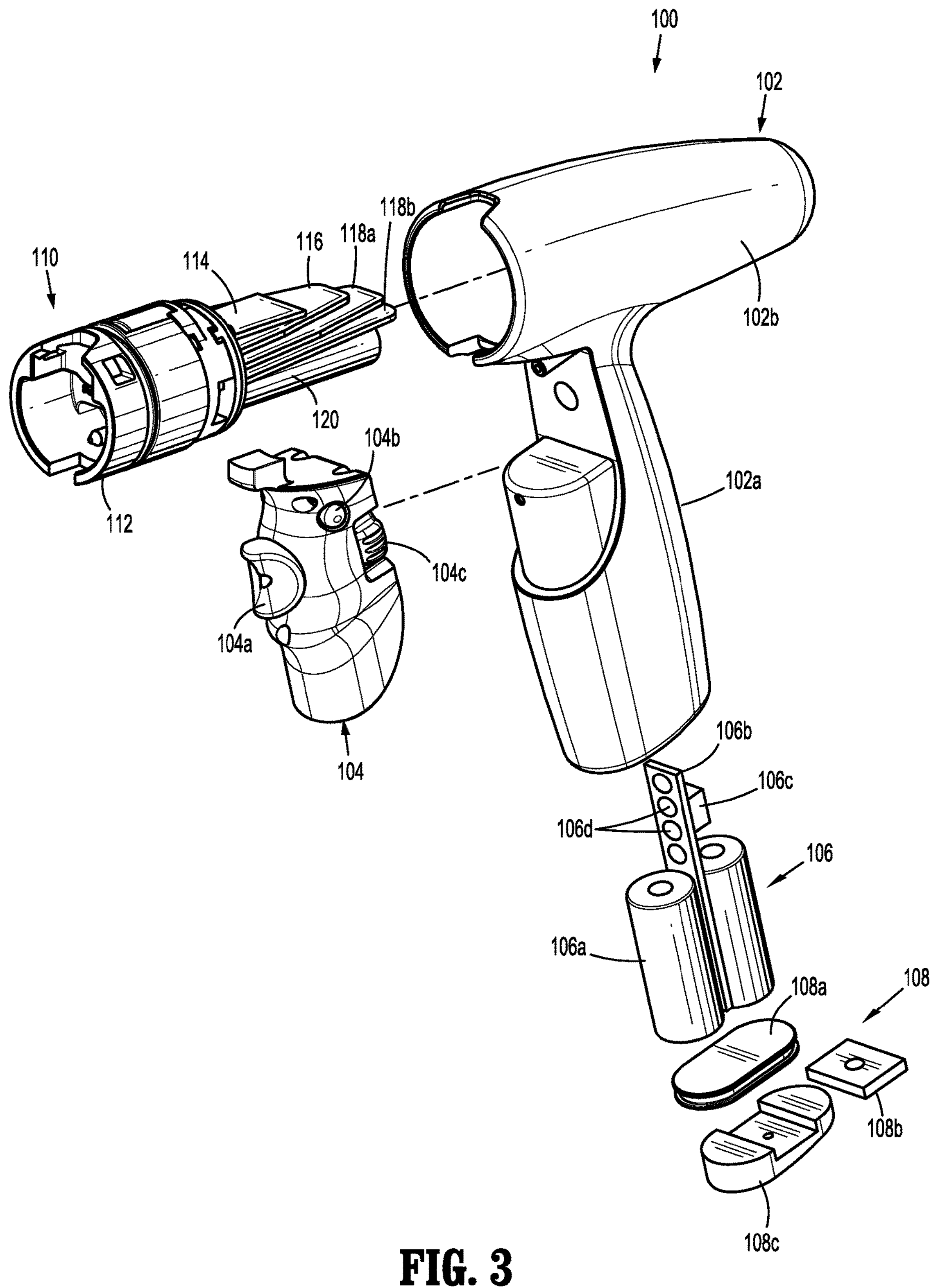
FIG. 3 is a perspective view, with parts separated, of a handle assembly of the electromechanical surgical system of FIG. 1.

As seen in FIG. 3, handle assembly 100 includes a handle housing 102 having a handle portion 102*a* and a body portion 102*b* extending transverse from body portion 102*a*. A switch block assembly 104 is removably mounted on handle portion 102*a* and includes various switches or actuators 104*a*-104*c* that are operable to activate some function of electromechanical surgical system 10 such as firing, rotation, articulation, and/or providing a safety lock. For example, as described in greater detail below, actuator 104*a* can be depressed to fire loading unit 300 (and/or end effector 302) while the components of electromechanical surgical system 10 are coupled together. In embodiments, one or more of actuators 104*a*-104*c* may be coupled to or support one or more magnets (not shown) for creating a magnetic field and/or communicating electrical signals to sensors disposed within handle and/or body portions 102*a*, 102*b* of handle assembly 100. A power assembly 106 is mounted in handle portion 102*a* by a sealing assembly 108. Power assembly 106 includes a battery pack 106*a* and a circuit board 106*b* that are electrically coupled to one another. Circuit board 106*b* can support any number or type of electrical components such as inductors 106*c*, sensors 106*d* (e.g., Hall Effect sensors), wires, chips, resistors, capacitors or the like. These electrical components may be in electrical communication with each other and/or with actuators 104*a*-104*c*.

Sealing assembly 108 is mounted to handle portion 102*a* and includes a sealing plate 108*a*, a twist lock plate 108*b*, and a cover plate 108*c* that couple together to support power assembly 106 within handle portion 102*a*.

A drive assembly 110, described in greater detail below, is supported in body portion 102*b* and includes a handle mount 112 that supports one or more antennae 114, 116 and one or more circuit boards 118*a*, 118*b* (e.g., with any number and/or type of electrical components as described above with respect to circuit board 106*b*) that are in electrical communication with power assembly 106. The antennae 114, 116 and/or circuit boards 118*a*, 118*b* (and/or circuit board 106*b*) may be wired and/or wirelessly coupled to one or more of any of the components of electromechanical surgical system 10. Handle mount 112 further supports a motor assembly 120 that is electrically coupled to antennae 114, 116 and/or circuit boards 118*a*, 118*b* which may function to activate motor assembly 120, or components thereof, upon actuation of one or more of switches 104*a*-104*c* of switch block assembly 104. The one or more antennae 114, 116 can be configured to electrically communicate (e.g., send and/or receive signals) with a remote system such as a cloud (not shown) and/or other remote system (e.g., a computer, robot, etc.).

Figure 4:
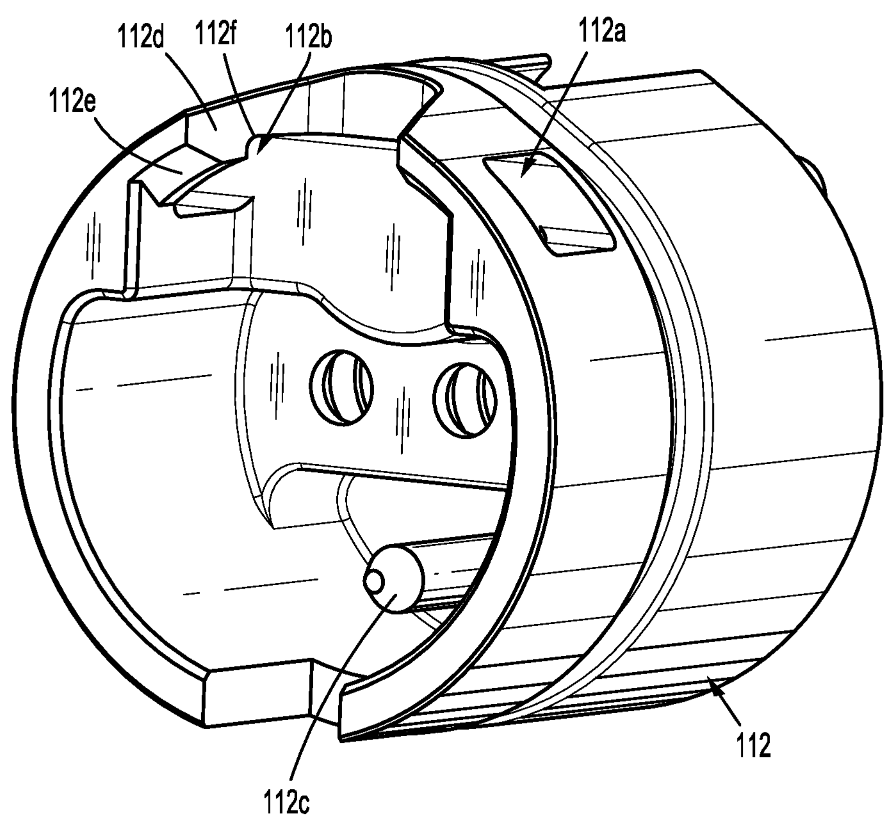
FIG. 4 is an enlarged perspective view of a handle mount of the handle assembly of FIG. 3.
Figure 5:
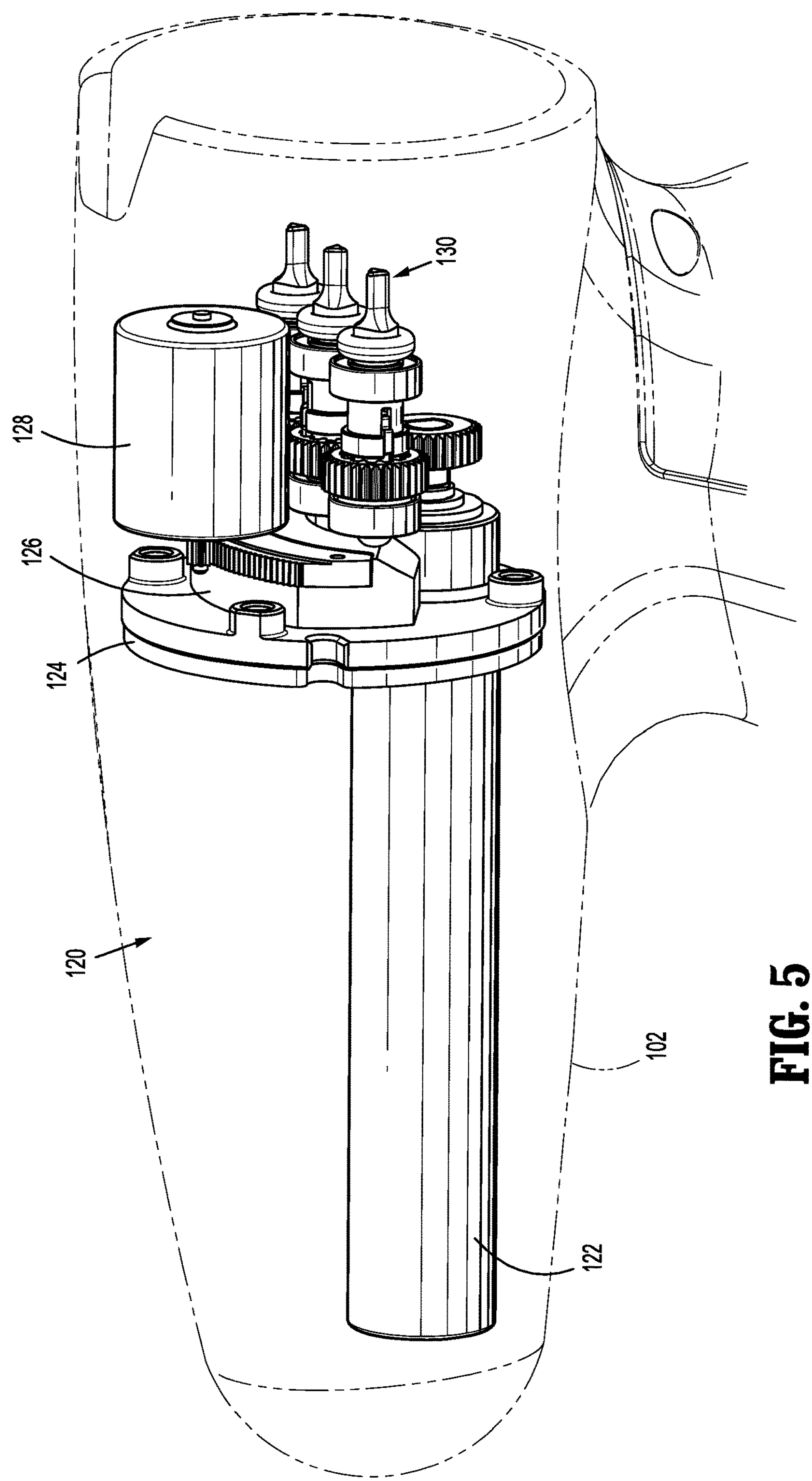
FIG. 5 is an enlarged perspective view of a motor assembly of the handle assembly of FIG. 3 with a handle housing of the handle assembly shown in phantom for clarity.
Figure 6:
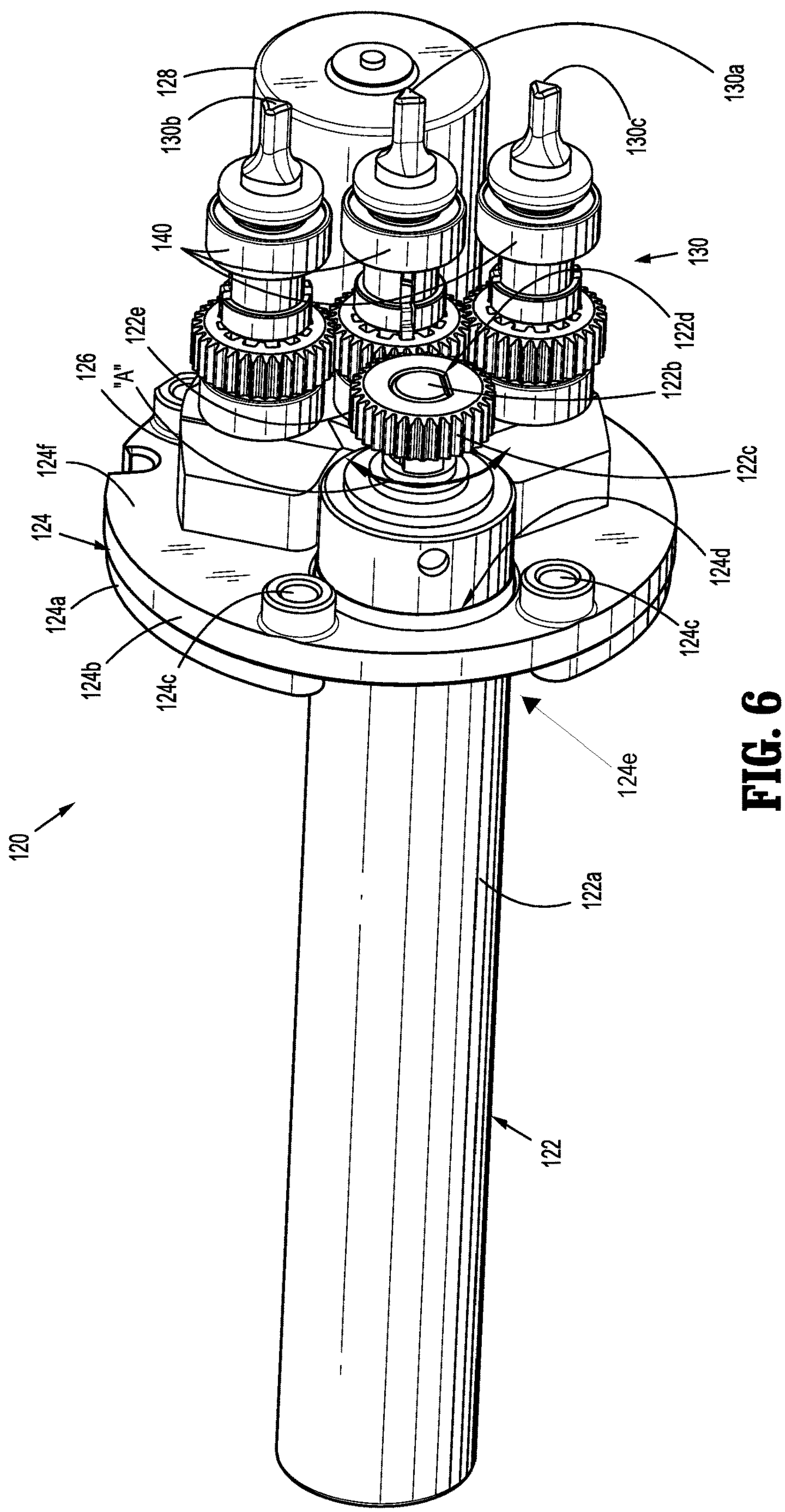
FIG. 6 is an enlarged perspective view of the motor assembly of FIG. 5.

As seen in FIG. 4, handle mount 112 defines first and second windows 112*a*, 112*b* therethrough and an alignment pin 112*c* that extends distally therefrom. An engagement tooth 112*d* is positioned distal to each of the respective first and second windows 112*a*, 112*b*. Each engagement tooth 112*d* defines a distal surface 112*e* that tapers proximally towards its respective window 112*a*, 112*b*. Each engagement tooth 112*d* further includes a proximal shoulder 112*f*.

For a more detailed description of similar surgical devices and components thereof that can be combined and/or interchanged with, or adapted for use with, the presently described electromechanical surgical systems 10, or components thereof, reference can be made to U.S. provisional patent application Ser. No. 62/066,996, filed on Oct. 22, 2014, International Publication. No. WO 2009/039506, and U.S. Patent Application Publication No. 2011/0121049, the entire contents of each of which are incorporated by reference herein.

Turning now to FIGS. 5-9, motor assembly 120 includes a drive motor assembly 122, mounting plates 124 supported on drive motor assembly 122, a selector cam 126 rotatably supported on drive motor assembly 122 adjacent mounting plates 124, a selector motor 128 coupled to selector cam 126, and an output assembly 130 coupled to drive motor assembly 122.

Drive motor assembly 122, which is electrically coupled to circuit boards 106*b*, 118*a*, 118*b* and/or antenna 116, includes a single motor 122*a*, a shaft 122*b* that extends distally from motor 122*a*, and a drive gear 122*c*. Shaft 122*b* has a non-circular cross-section. The cross-section of shaft 122*b* may have any suitable cross-sectional configuration (e.g., star, triangle, hexalobular, D-shape, etc.). Drive gear 122*c* defines an opening 122*d* that receives shaft 122*b* of drive motor assembly 122 so that drive gear 122*c* rotates with shaft 122*b*, as indicated by arrow "A," upon actuation of motor 122*a*. Opening 122*d* may have any suitable configuration. In embodiments, opening 122*d* complements the cross-section of shaft 122*b*. Drive gear 122*c* further defines teeth 122*e* around an outer surface thereof that engage output shaft assembly 130 to impart drive force from motor 122*a* thereon.

Mounting plates 124 include first and second mounting plates 124*a*, 124*b* that are secured together using any known fastening technique such as welding, fastening, press-fit, etc. For example, first and second mounting plates 124*a*, 124*b* can be secured together by fasteners 124*c*. Drive motor assembly 122 extends through an enlarged first aperture 124*e* formed in first mounting plate 124*a* and a second aperture 124*d* defined in second mounting plate 124*b* to receive motor 122*a* of drive motor assembly 122 therein and to support drive motor assembly 122.

Figure 9:
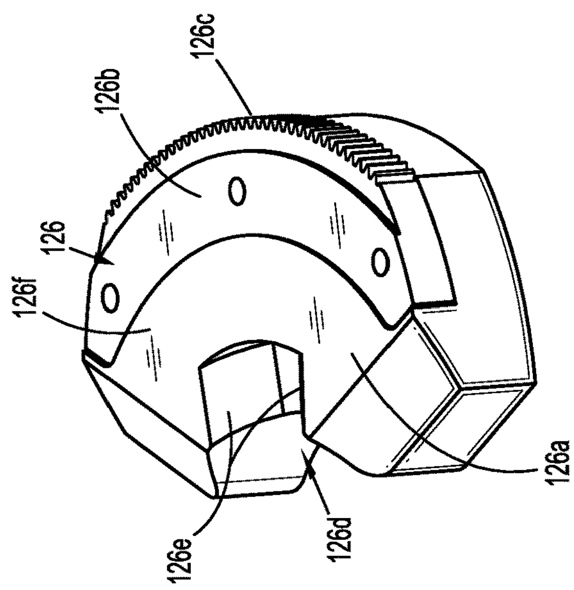
FIG. 9 is an enlarged perspective view of a selector cam of the motor assembly of FIGS. 5-7.

Selector cam 126 is coupled to selector motor 128 and mounted on drive motor assembly 122 adjacent to, and in contact with, a distal surface 124*f* of second mounting plate 124*b*. As indicated by arrow "B" seen in FIG. 7, selector cam 126 rotates radially around drive motor assembly 122, as described in greater detail below. With reference to FIG. 9, selector cam 126 includes a body portion 126*a* and a gear portion 126*b*. Gear portion 126*b* is secured to, or otherwise formed in, body portion 126*a* and includes teeth 126*c* extending therefrom. Teeth 126*c* are shown arranged in an arcuate configuration about gear portion 126*b*, but may be arranged in any suitable configuration. Body portion 126*a* of selector cam 126 defines a recess 126*d* having tapered sidewalls 126*e*. Body portion 126*a* further includes a compression surface 126*f* positioned between gear portion 126*b* and recess 126*d*.

Figure 7:
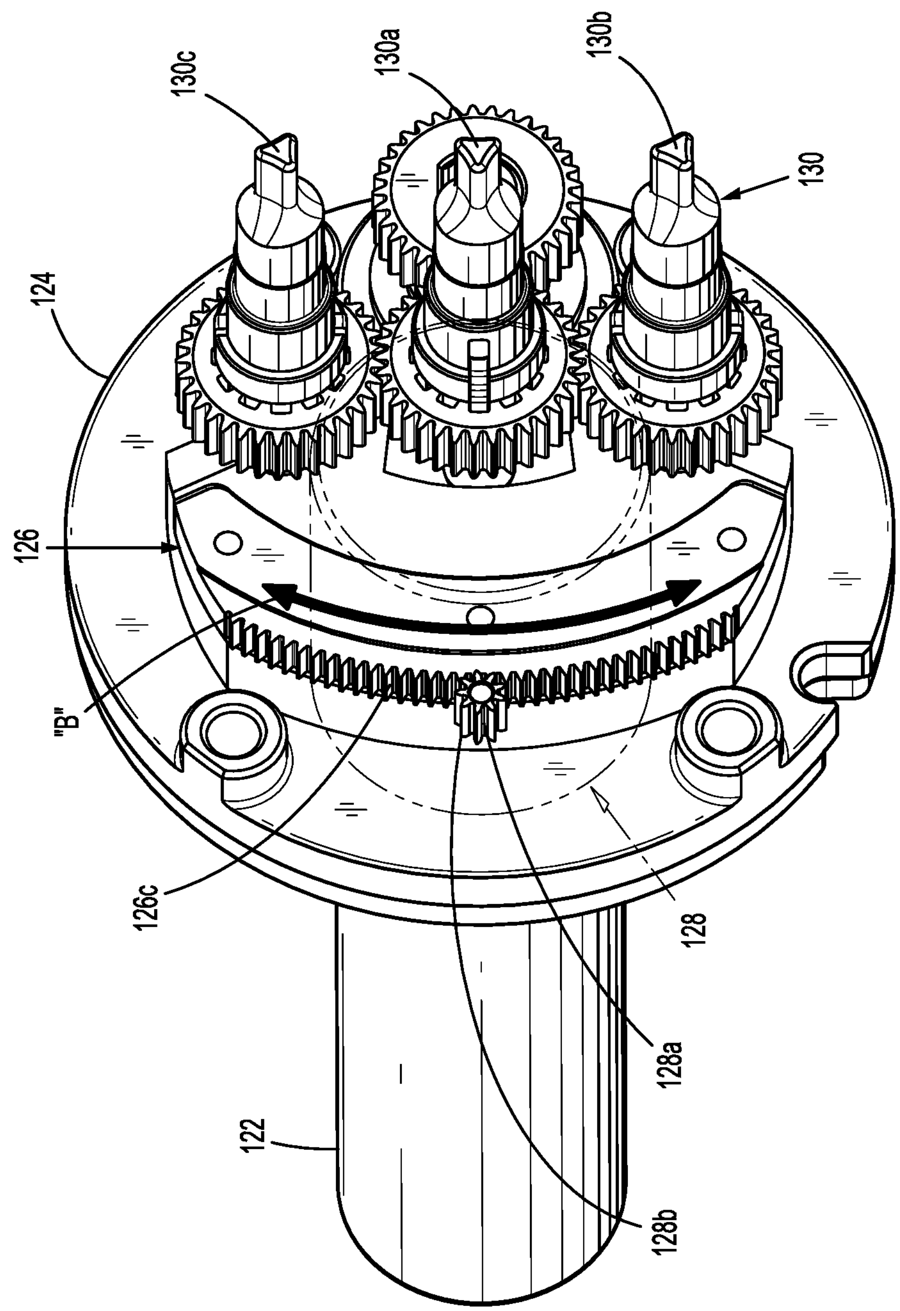
FIG. 7 is an enlarged perspective view of the motor assembly of FIGS. 5 and 6 with a selector motor thereof shown in phantom for clarity.

As seen in FIG. 7, selector motor 128 includes, or rotatably supports, a selector gear 128*a* having teeth 128*b* that are engaged with teeth 126*c* of selector cam 126. Selector motor 128 rotates selector gear 128*a* to rotate selector cam 126 between first, second, and third positions about drive motor assembly 122, as described in greater detail below.

Figure 8:
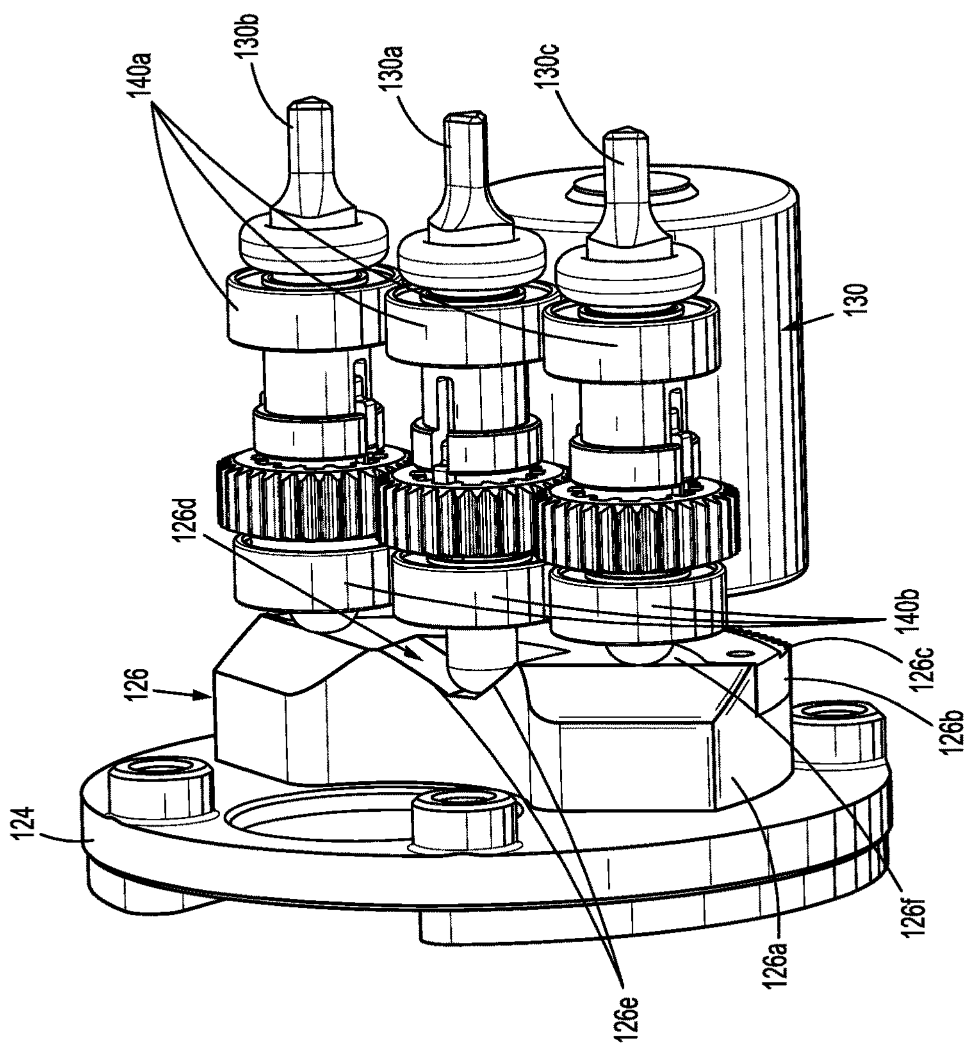
FIG. 8 is an enlarged perspective view of a distal portion of the motor assembly of FIGS. 5 and 6 with a drive motor thereof removed for clarity.

Referring also to FIG. 8, motor assembly 120 includes an output assembly 130 having a first output assembly 130*a*, a second output assembly 130*b*, and a third output assembly 130*c*.

Figure 12:
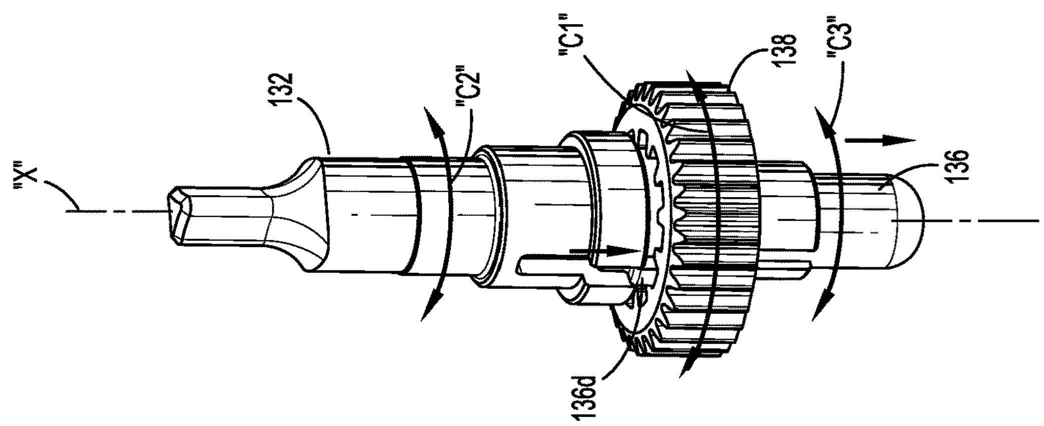
FIGS. 11 and 12 are progressive views of the output assembly of FIG. 10 illustrating the output assembly moving between first and second positions.
Figure 11:
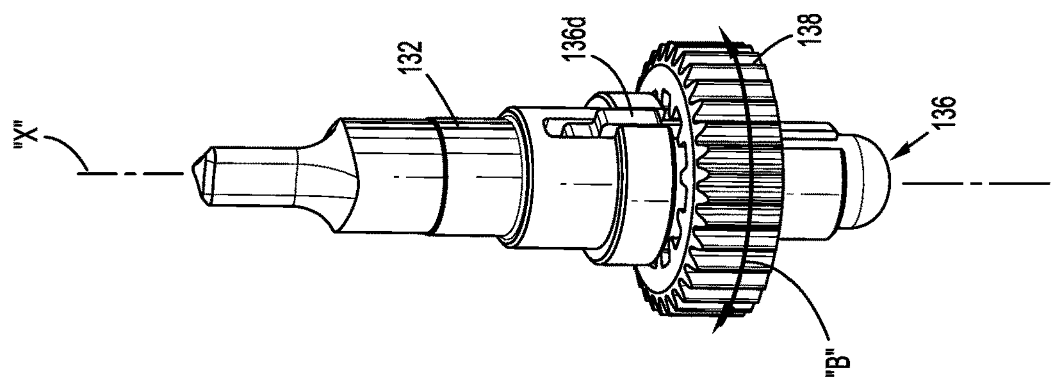
Figure 10:
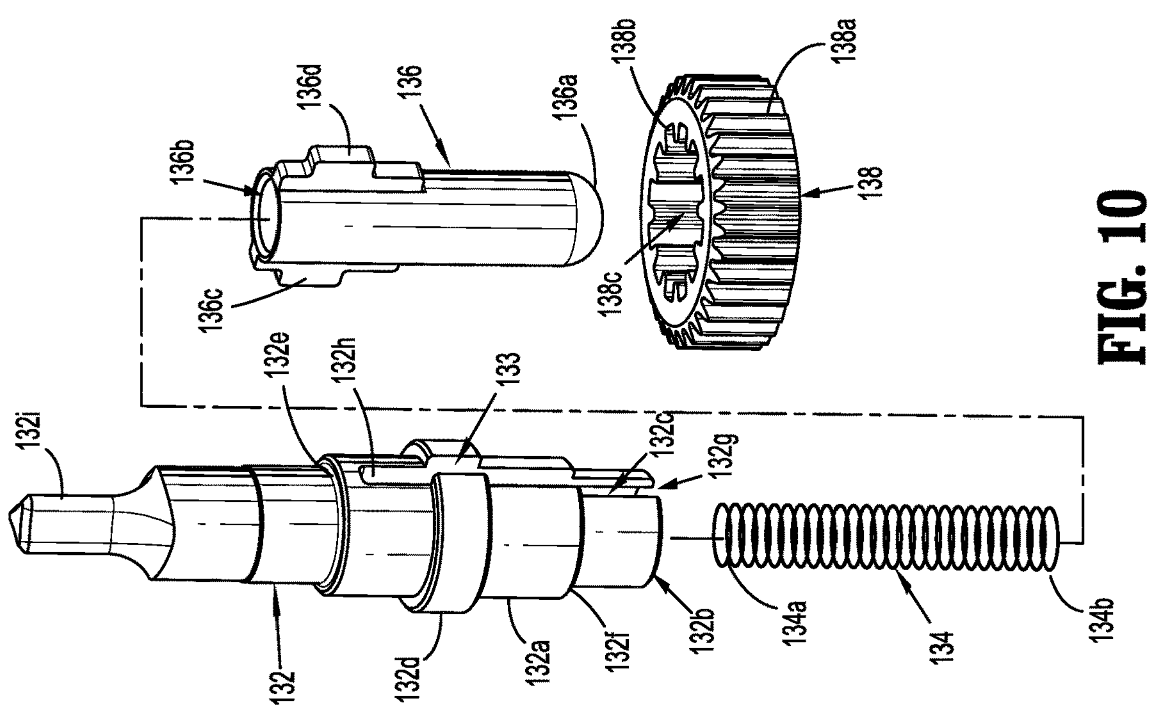
FIG. 10 is a perspective view, with parts separated, of an output assembly of the motor assembly of FIGS. 5-7.

With reference to FIGS. 10-12, each of the first, second, and third output assemblies 130*a*, 130*b*, 130*c* (see FIGS. 7 and 8) defines a longitudinal axis "X" and includes a respective output shaft 132, spring 134, engagement key 136, and output gear 138. Output shaft 132 includes a shaft body 132*a* that defines a spring bore 132*b* therein and a slot 132*c* therealong. Spring bore 132*b* of output shaft 132 receives a first end 134*a* of spring 134 therein. Shaft body 132*a* of output shaft 132 includes first, second, and third annular shoulders 132*d*, 132*e*, 132*f* that extend radially around an outer surface thereof at spaced apart locations relative to one another. First annular shoulder 132*d* of shaft body 132*a* is positioned between second and third shoulders 132*e*, 132*f* and functions to limit axial movement of output gear 138 along shaft body 132*a*. Second annular shoulder 132*e* of shaft body 132*a* is positioned distal to first and third annular shoulders 132*d*, 132*f* and functions to support a distal bearing 140*a* thereon. Third annular shoulder 132*e* of shaft body 132*a* is positioned proximal to first and second shoulders 132*f* and functions to support a proximal bearing 140*b* thereon (see, e.g., FIG. 8). Slot 132*c* of output shaft 132 extends from an open proximal end 132*g* of shaft body 132*a* that receives spring 134, and through shoulder 132*d* to separate shoulder 132*d* into two separate and discrete sections with a coupling region 133 for engagement key 136 defined therebetween. Slot 132*c* of output shaft 132 opens through opposite side surfaces of shaft body 132*a* and includes a closed distal end 132*h* adjacent to, and proximal of, second shoulder 132*e*.

Output shaft 132 includes a driver head 132*i* that extends distally from shaft body 132*a*. Driver head 132*i* can have any suitable non-circular configuration such as a triangular configuration, square configuration, hexalobular configuration, etc.

Engagement key 136 of each output assembly 130 includes a rounded tip 136*a* at a proximal end thereof and defines a spring bore 136*b* in a distal end thereof. Spring bore 136*b* receives a second end 134*b* of spring 134 therein to support spring 134 between output shaft 132 and engagement key 136. Engagement key 136 further includes flanges 136*c*, 136*d* that extend laterally outward from side surfaces of the distal end of engagement key 136. Flanges 136*c*, 136*d* of engagement key 136 are slidable through slot 132*c* of output shaft 132 on opposite sides of output shaft 132. Spring 134 is configured to bias engagement key 136 in a proximal direction (e.g., away from output shaft 132) toward selector cam 126.

Output gear 138 of each output assembly 130 includes outer teeth 138*a* that extend from an outer surface thereof, and inner teeth 138*b* that extend from an inner surface thereof into an opening 138*c* defined through output gear 138. Adjacent inner teeth 138*b* of output gear 138 are spaced to selectively receive flanges 136*c*, 136*d* of engagement key 136 therein.

As described in greater detail below, in a disengaged position (e.g., unlocked) of engagement key 136 with respect to output gear 138, flanges 136*c*, 136*d* of engagement key 136 are longitudinally offset from, and distal to, inner teeth 138*b* of output gear 138 relative to longitudinal axis "X," as seen in FIG. 11, such that output gear 138 can rotate about, and relative to, longitudinal axis "X," engagement key 136, and output shaft 132, as indicated by arrows "B." Specifically, output gear 138 is independent of engagement key 136 and output shaft 132, when engagement key 136 is in the disengaged position.

In an engaged position (e.g., locked) of engagement key 136 with respect to output gear 138, as seen in FIG. 12, flanges 136*c*, 136*d* of engagement key 136 are partially disposed between inner teeth 138*b* of output gear 138 (e.g., partially longitudinally aligned relative to longitudinal axis "X") while partially positioned within coupling region 133 of shoulder 132*d* of output shaft 132. In the engaged position of engagement key 136, output shaft 132 and output gear 138 are locked and movable together. More specifically, output shaft 132, engagement key 136, and output gear 138 rotate together about longitudinal axis "X," as indicated by arrows "C1," "C2," and "C3."

Figure 13:
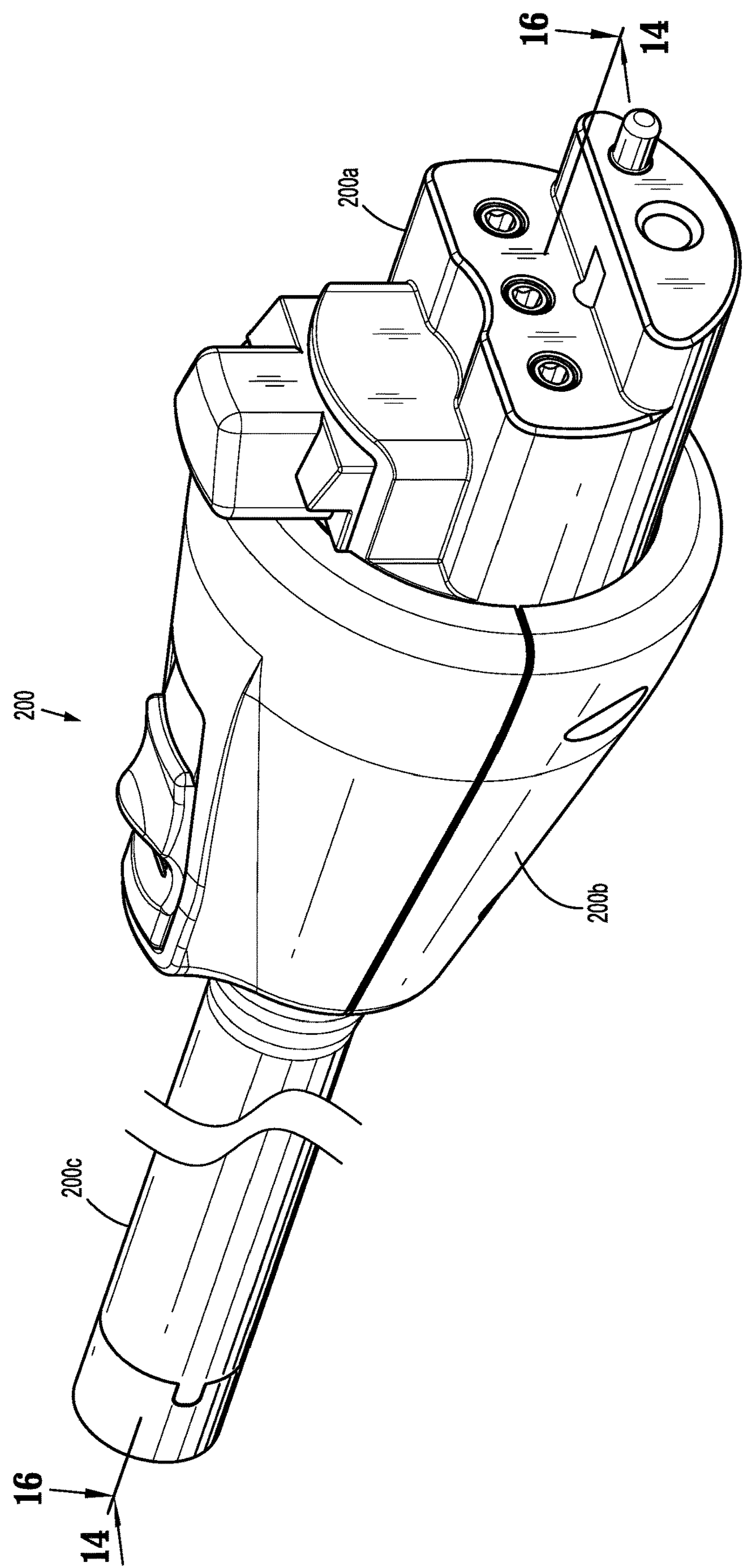
FIG. 13 is an enlarged, rear, perspective view of an adapter assembly of the electromechanical surgical system of FIG. 1.

Turning now to FIG. 13, adapter assembly 200 includes a proximal housing 200*a* at a proximal end of adapter assembly 200. The proximal end of proximal housing 200*a* selectively secures to a distal end of handle assembly 100. Adapter assembly 200 includes a distal housing 200*b* that extends distally from proximal housing 200*a* and an outer tube 200*c* that extends distally from distal housing 200*b* to a distal end.

Figure 14:
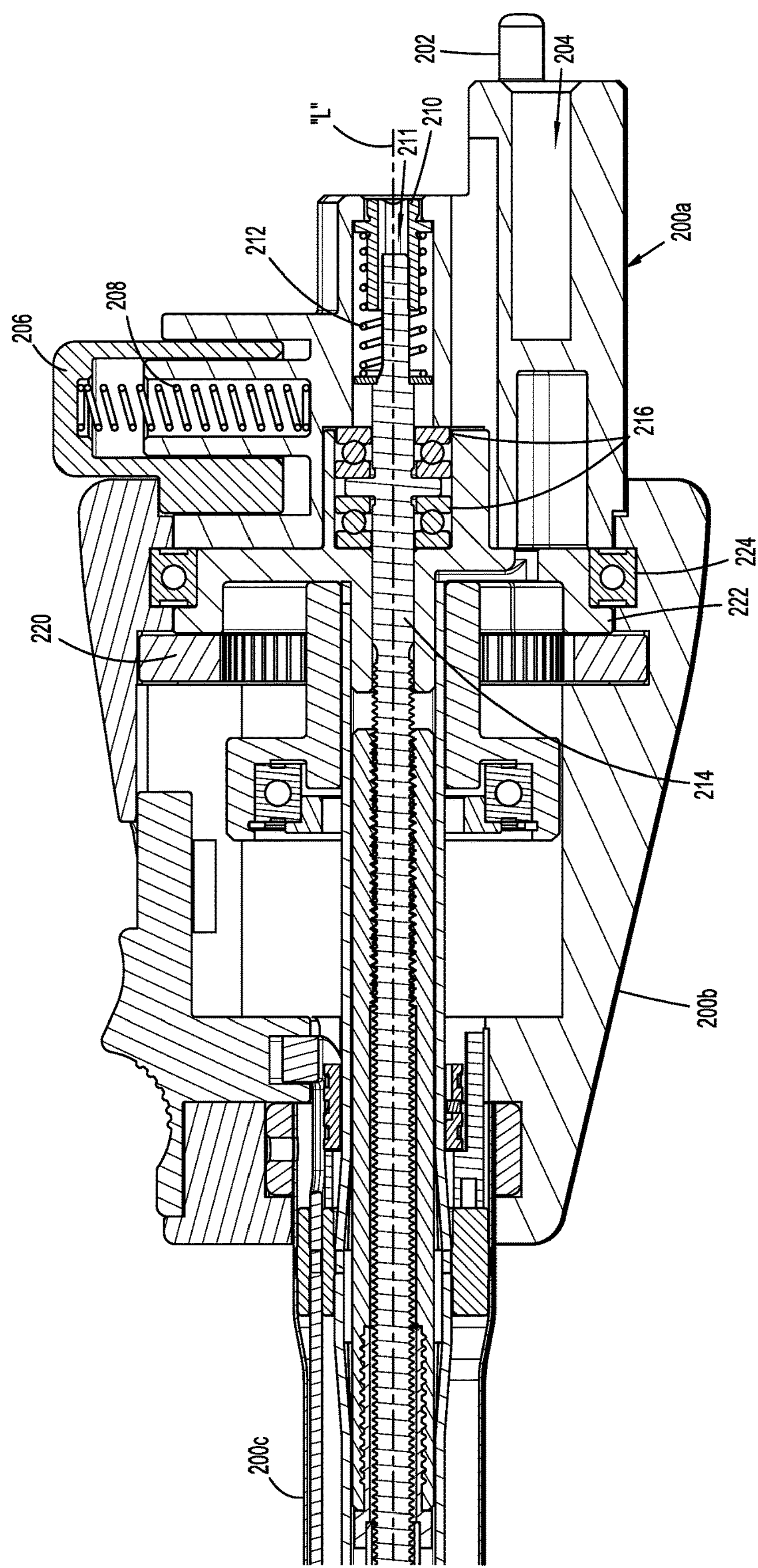
FIG. 14 is a cross-sectional view of the adapter assembly of FIG. 13 as taken along section line 14-14 shown in FIG. 13.
Figure 15:
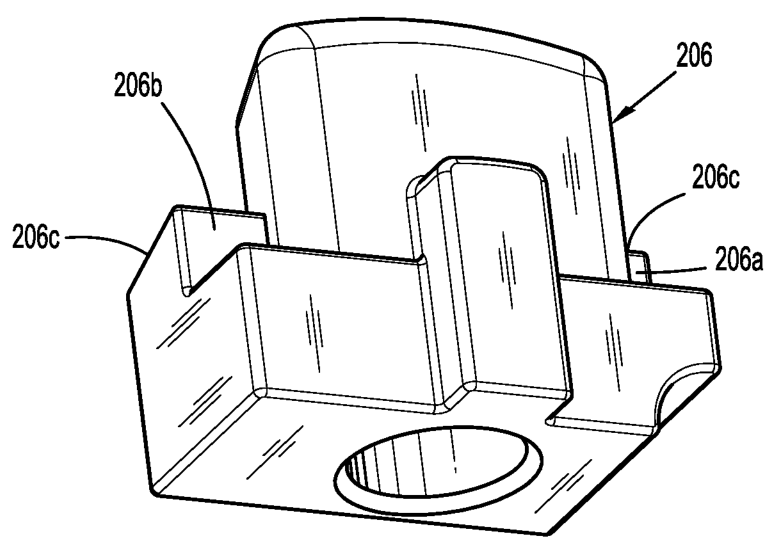
FIG. 15 is an enlarged perspective view of an adapter release button of the adapter assembly of FIG. 13.
Figure 19:
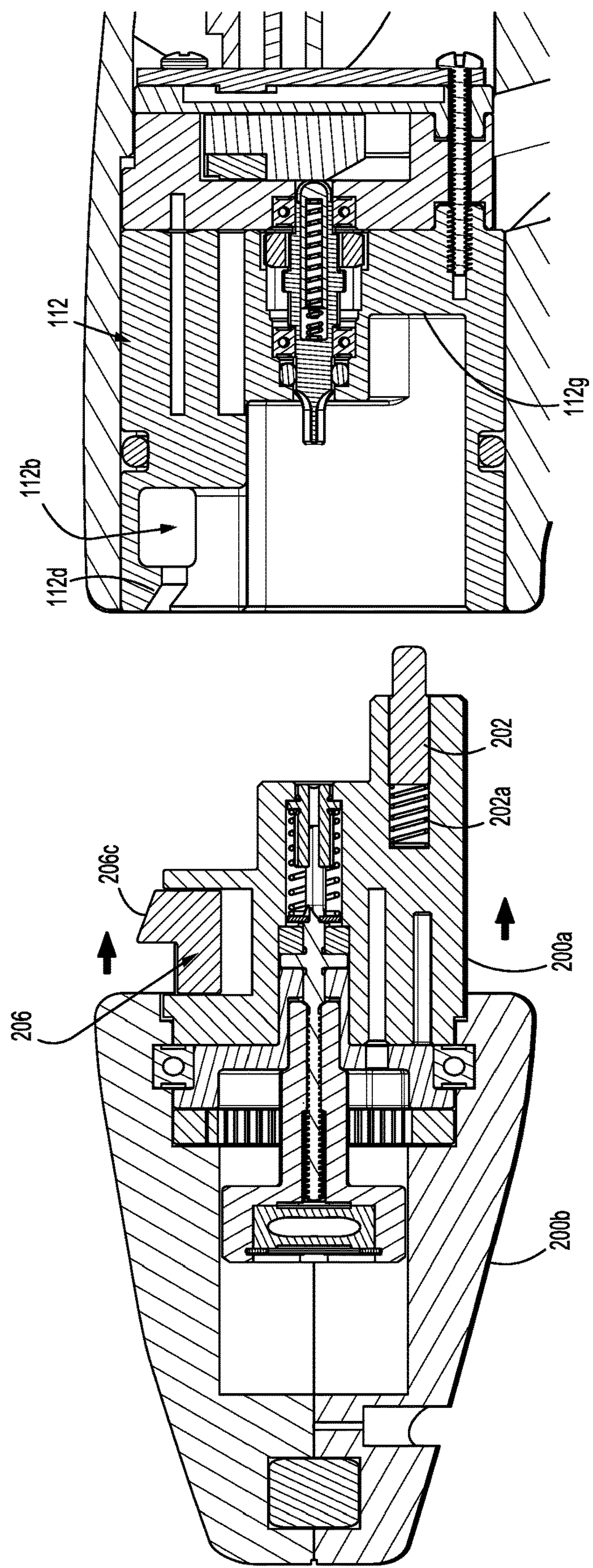
Figure 20:
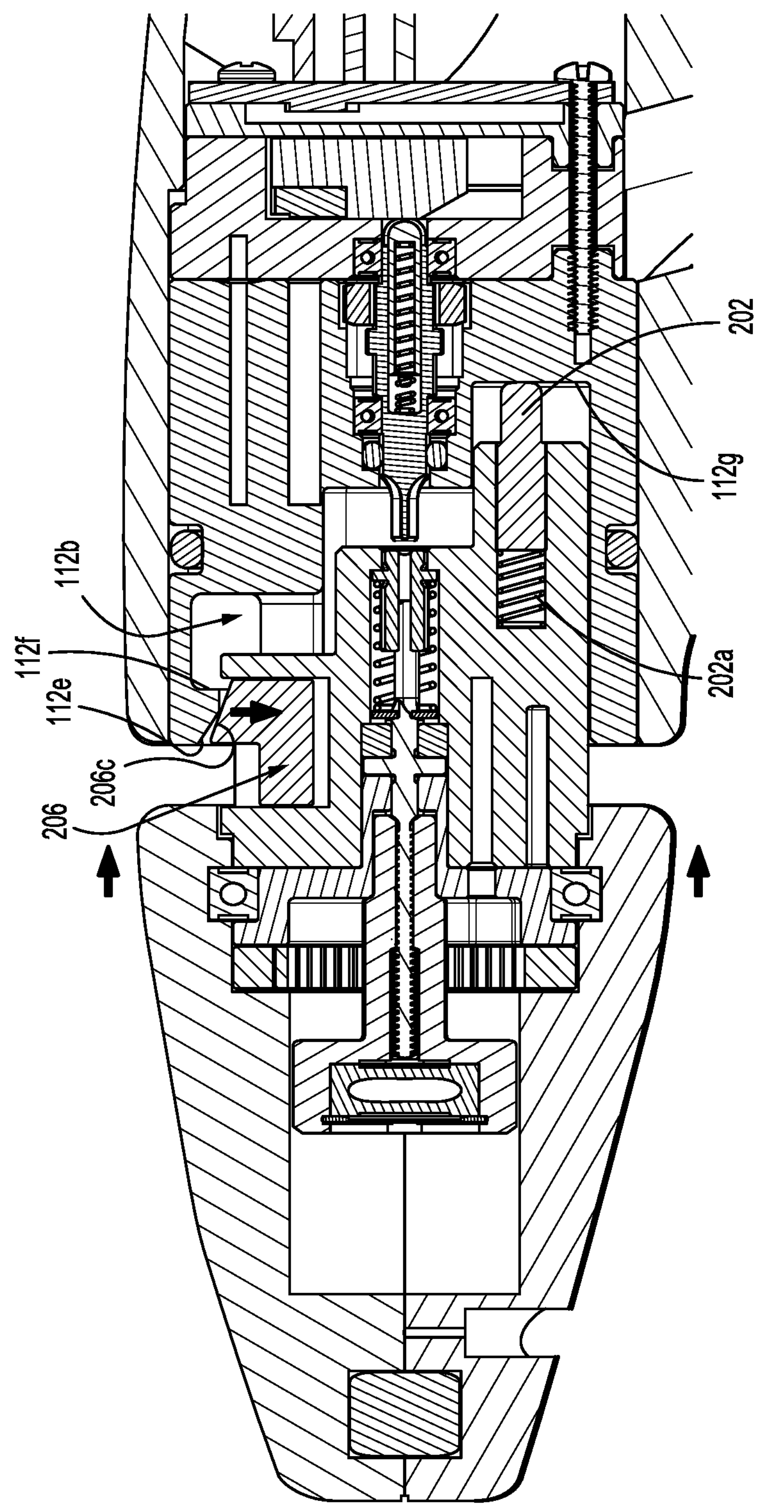
Figure 21:
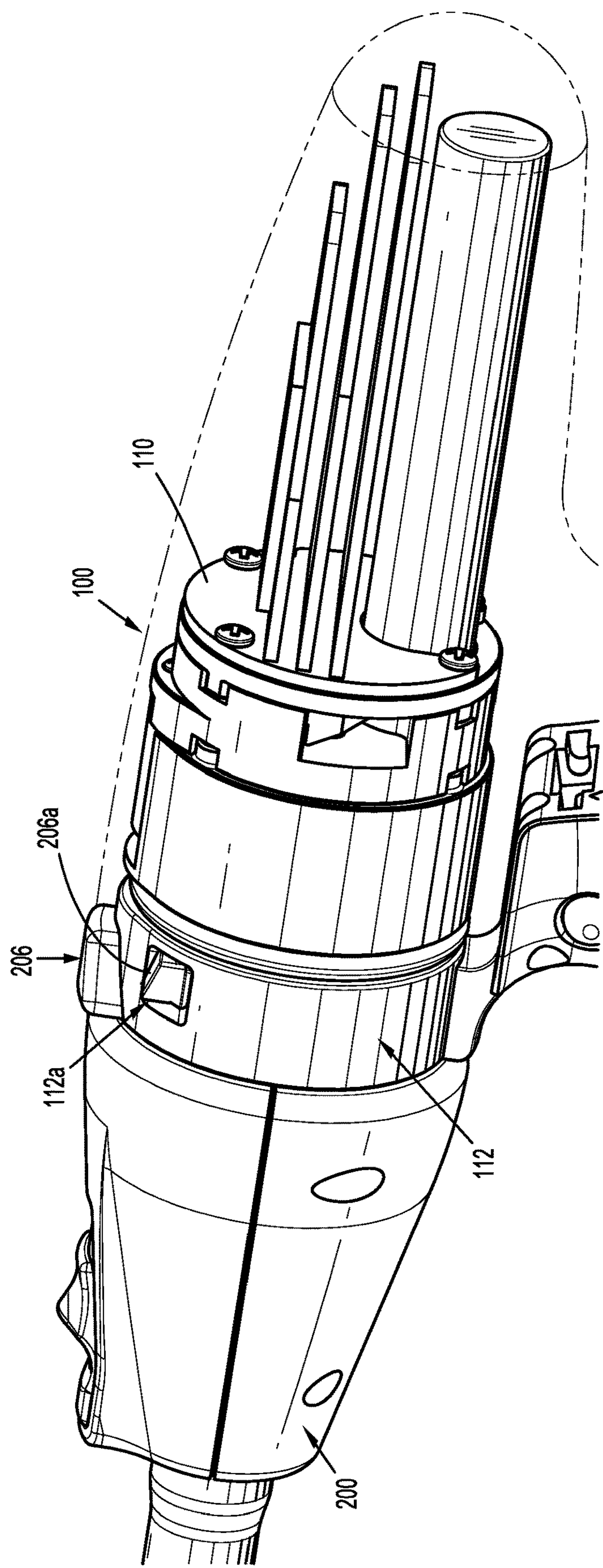
Figure 22:
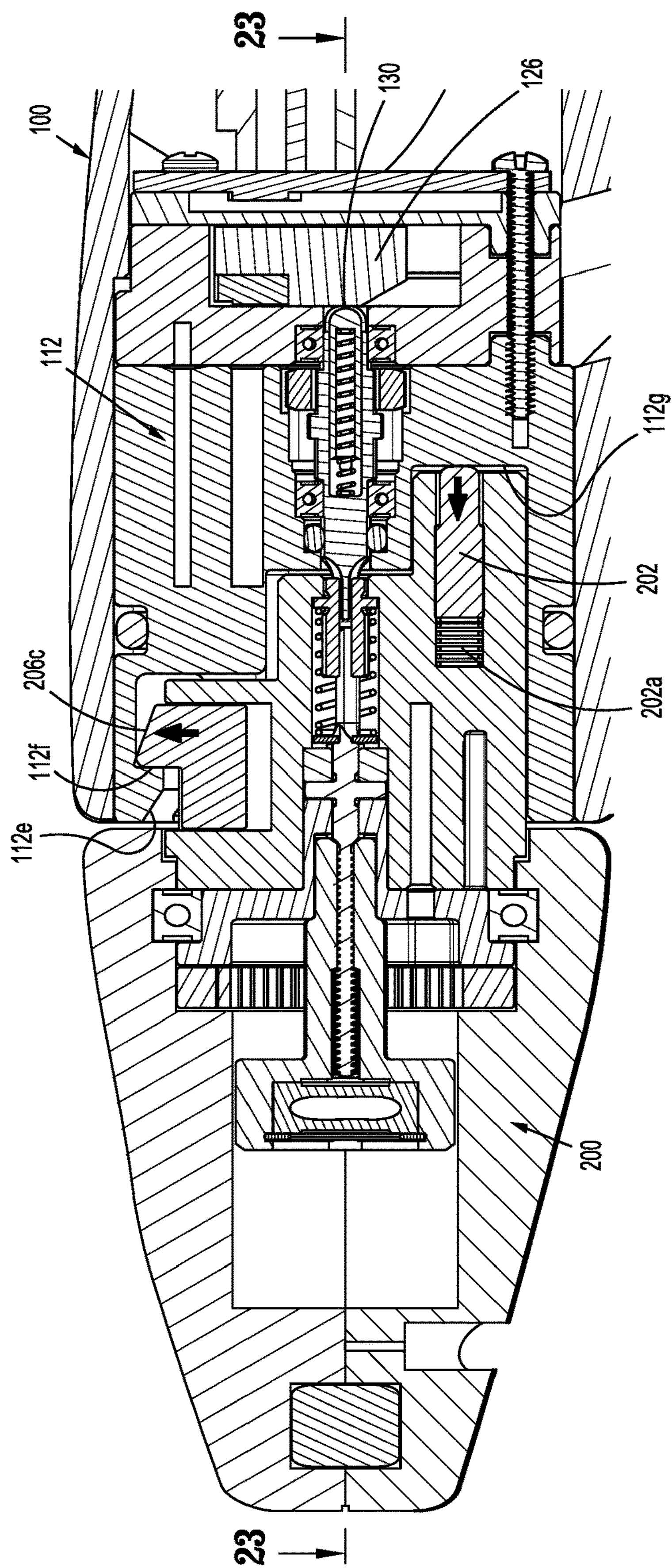
Figure 23:
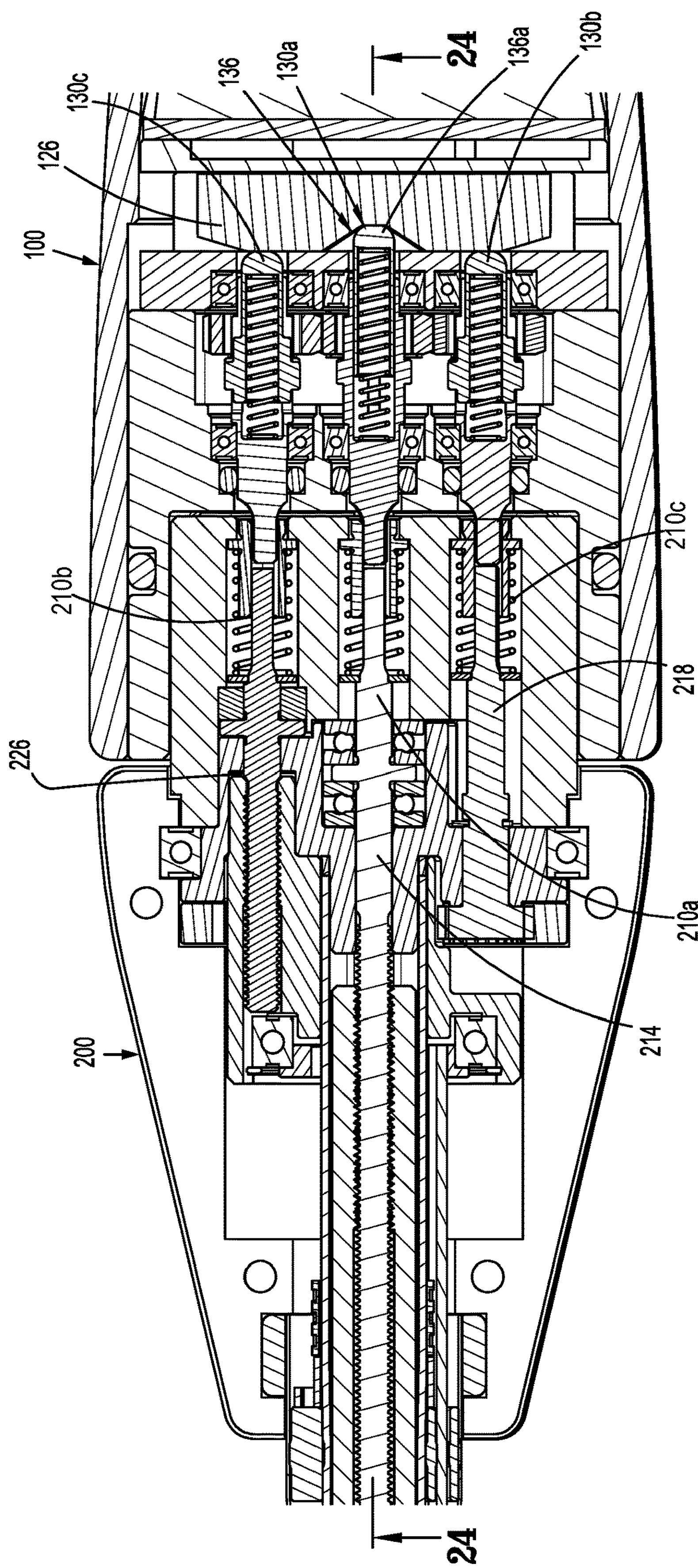
Figure 24:
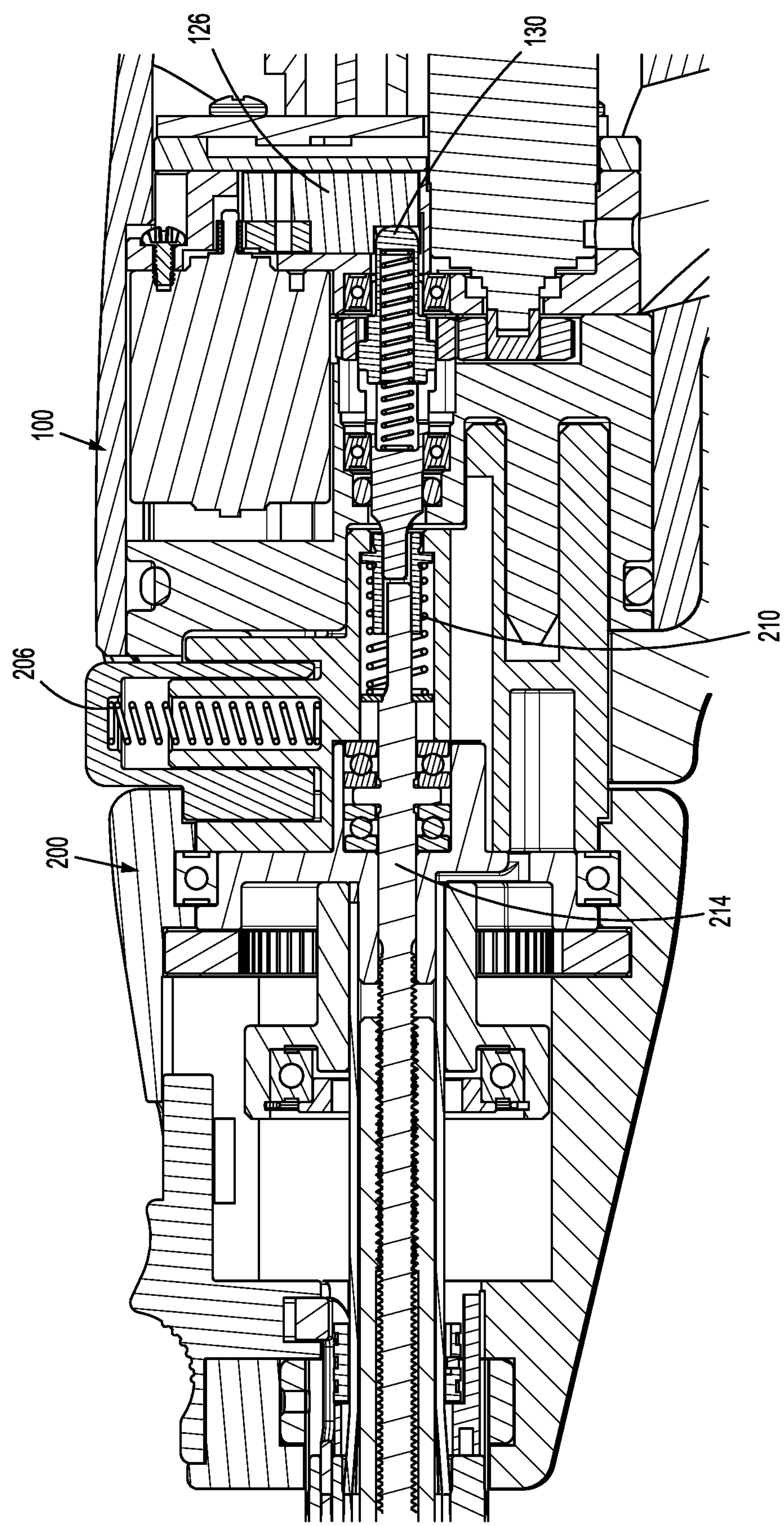

With reference to FIG. 14, proximal housing 200*a* of adapter assembly 200 supports an ejector pin 202 that is spring biased by a spring 202*a* (see FIG. 19). Proximal housing 200*a* defines an alignment bore 204 that receives alignment pin 112*c* of handle mount 112 during coupling of adapter assembly 200 to handle assembly 100 (see FIG. 17). Proximal housing 200*a* further supports a spring loaded button 206 that is spring biased by a spring 208. As seen in FIG. 15, spring loaded button 206 includes nubs 206*a*, 206*b* that extend to angled surfaces 206*c*. Nubs 206*a*, 206*b* are receivable within windows 112*a*, 112*b* of handle mount 112 (see FIG. 4), respectively, to secure adapter assembly 200 to handle assembly 100 as described in greater detail below.

Figure 16:
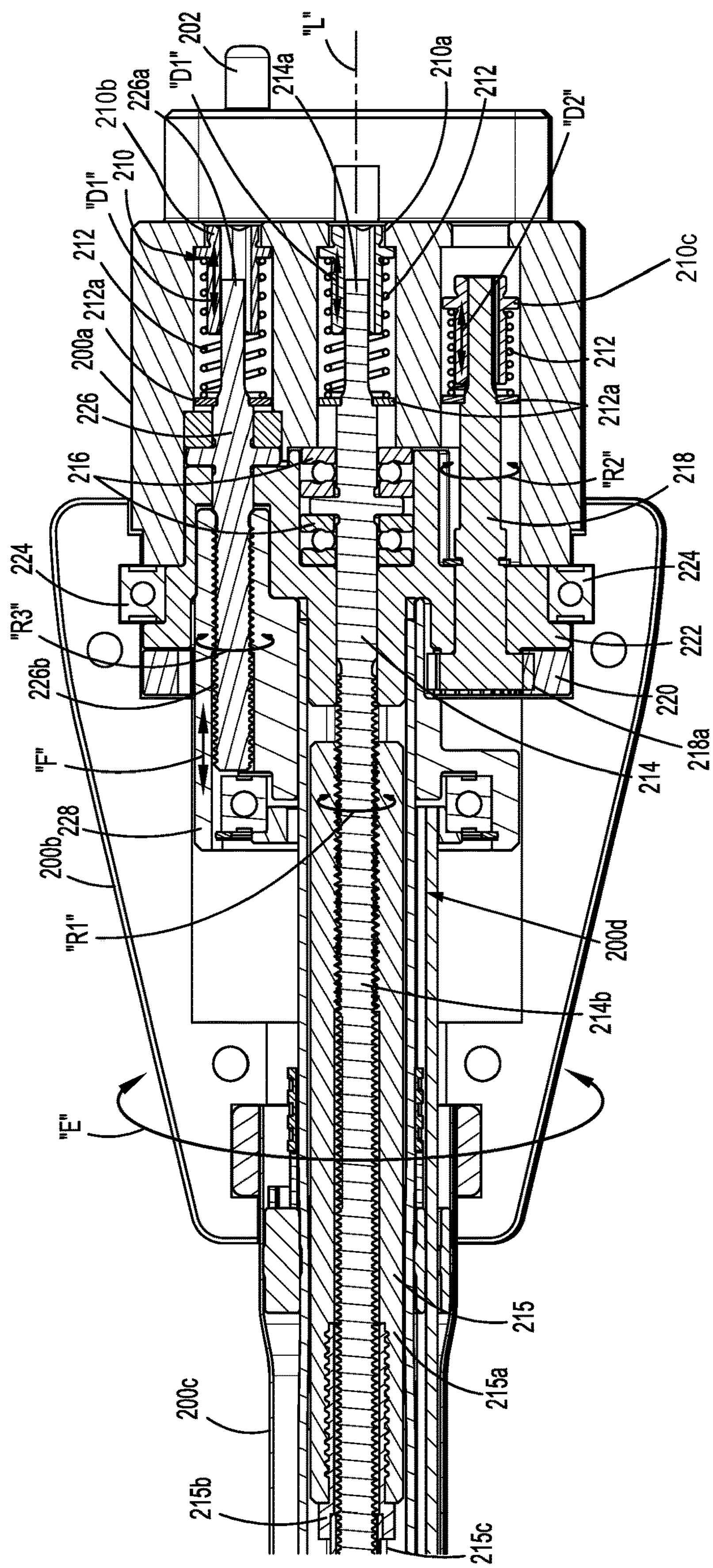
FIG. 16 is a cross-sectional view of the adapter assembly of FIG. 13 as taken along section line 16-16 shown in FIG. 13.
Figure 17:
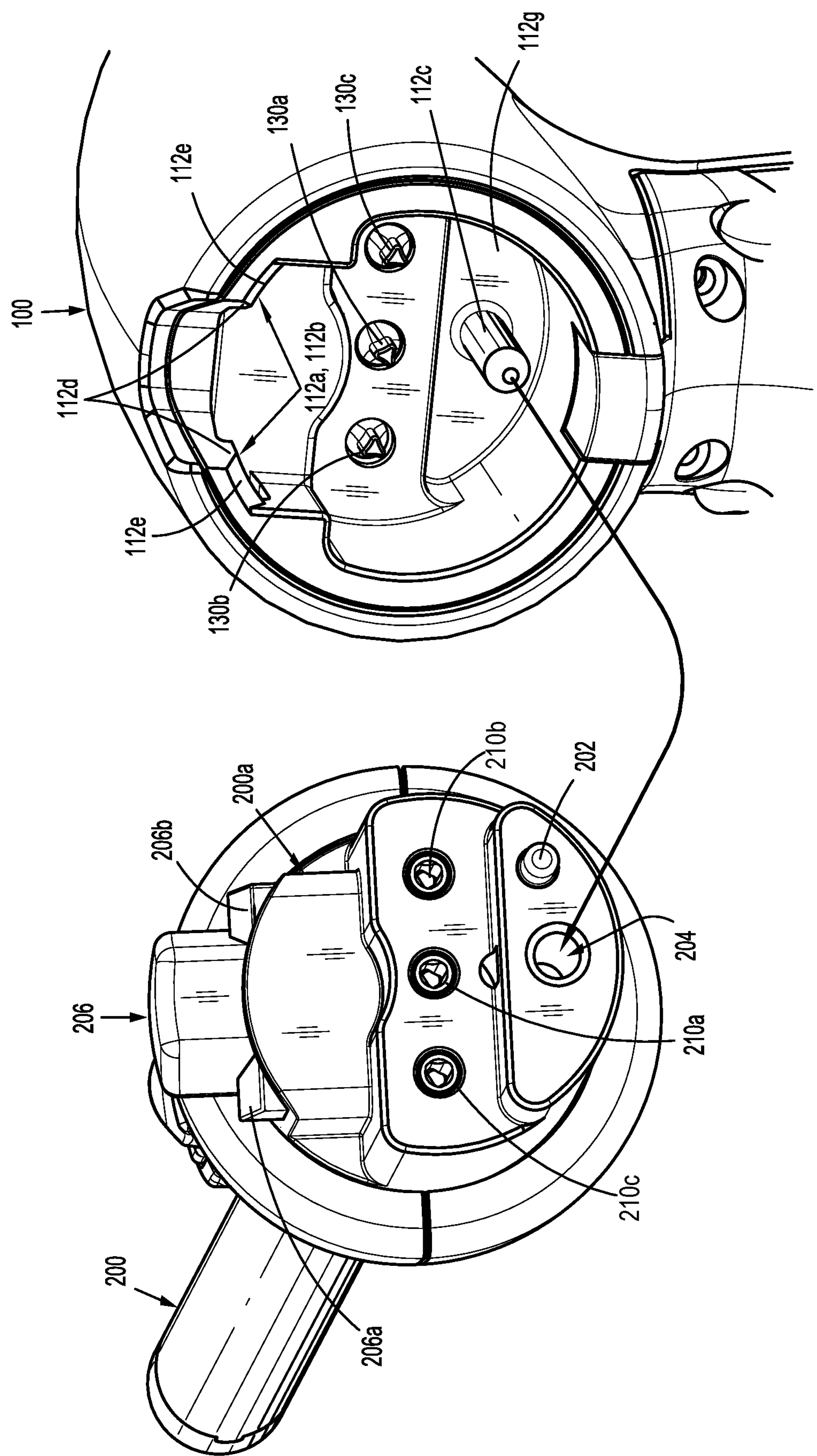
FIG. 17 is a perspective view, with parts separated, of the handle and adapter assemblies of FIGS. 3 and 13.
Figure 18:
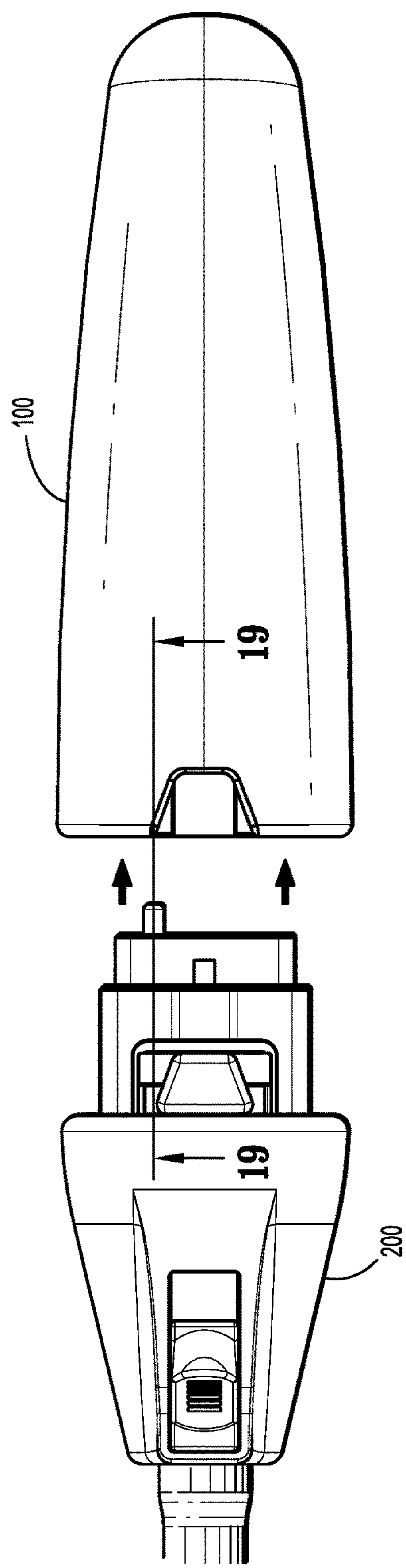
FIGS. 18-24 are progressive views showing the adapter assembly of FIG. 13 being connected to the handle assembly of FIG. 3.

Referring also to FIG. 16, input couplers 210 of adapter assembly 200 include first, second, and third input couplers 210*a*, 210*b*, 210*c* that are supported by proximal housing 200*a* and are spring biased in a proximal direction, as indicated by arrows "D1," by springs 212 coupled to rotation mounts 212*a*. As indicated by arrows "D2," springs 212 can be compressed in a distal direction against biasing forces of springs 212. As seen in FIG. 14, each input coupler 210 defines a non-circular passage 211 therethrough that may have any suitable cross-sectional configuration (e.g., star, triangle, hexalobular, D-shape, etc.). With reference to FIG. 17, first, second, and third input couplers 210*a*, 210*b*, 210*c* are positioned to complement output shafts 130*a*, 130*b*, 130*c* of handle assembly 100, respectively.

With continued reference to FIG. 16, first input coupler 210*a* is coupled to a proximal segment 214*a* of a firing shaft 214 of adapter assembly 200 and is rotatable with first input coupler 210*a*, as indicated by arrows "R1." Firing shaft 214 is supported by bearings 216 disposed in distal housing 200*b* and includes a threaded distal segment 214*b* having proximal and distal ends. The proximal end of threaded distal segment 214*b* is coupled to a threaded sleeve assembly 215, and the distal end of threaded distal segment 214*b* is coupled to loading unit 300 (and/or end effector 302).

Threaded sleeve assembly 215 includes a support sleeve 215*a* threadably coupled to a tension sleeve 215*b*. Tension sleeve 215*b* can be coupled to connecting members 215*c* (e.g., cables, rods, etc.) that extend distally to a distal end of outer tube 200*c* to manipulate the distal end of outer tube 200*c* of adapter assembly 200 when coupled to loading unit 300 (and/or end effector 302). For example, connecting members 215*c* may couple to a gimbal (not shown) or the like to facilitate articulation of loading unit 300 (and/or end effector 302) relative to adapter assembly 200. A more detailed description of an exemplary gimbal that can be used with, or adapted for use with, the presently described electromechanical surgical system 10, reference can be made to U.S. patent application Ser. No. 14/257,063, filed on Apr. 21, 2014, the entire contents of which are hereby incorporated by reference herein.

Second input coupler 210*b* of adapter assembly 200 is coupled to a rotation shaft 218 of adapter assembly 200 and, as indicated by arrows "R2," rotation shaft 218 is rotatable with second input coupler 210*b*. Rotation shaft 218 includes a rotation gear 218*a* supported on a distal end of rotation shaft 218. Rotation gear 218*a* is engaged with a rotation ring gear 220 secured to distal housing 200*b*. Rotation shaft 218 is further supported in distal housing 200*b* by a support frame 222 and a rotation bearing 224. Rotation bearing 224 enables distal housing 200*b* to rotate in response to simultaneous rotation of second input coupler 210*b* and rotation shaft 218. In use, with distal housing 200*b* secured to outer tube 200*c*, and outer tube 200*c* coupled to loading unit 300 (and/or end effector 302), rotation of distal housing 200*b* rotates loading unit 300 (and/or end effector 302) about longitudinal axis "L," as indicated by arrows "E."

Third input coupler 210*c* of adapter assembly 200 is coupled to a proximal end 226*a* of an articulation shaft 226 that is rotatable with third input coupler 210*c*, as indicated by arrows "R3." A distal end 226*b* of articulation shaft 226 is threadably coupled to an articulation sleeve 228 secured to a proximal end of an inner tube 200*d*. A distal end of inner tube 200*d* of adapter assembly 200 is operatively coupled to loading unit 300 (and/or end effector 302). In response to rotation of articulation shaft 226, articulation sleeve 228 is axially slidable along longitudinal axis "L," as indicated by arrows "F," to perform a function such as articulation of loading unit 300 (and/or end effector 302) relative to adapter assembly 200.

The proximal ends of threaded firing shaft 214, rotation shaft 218, and/or articulation shaft 226, may have any suitable cross-sectional configuration (e.g., star, triangle, hexalobular, D-shape, etc.) and may complement the non-circular passages 211 of respective input couplers 210 to enable input couplers 210 to slide along proximal ends of respective shafts 214, 218, 226 when springs 212 are positioned between compressed (see, e.g., spring 212 of input coupler 210*b* in FIG. 16) and uncompressed conditions (see, e.g., springs 212 of input couplers 210*a*, 210*c* in FIG. 16), for example, to facilitate a coupling and/or uncoupling of handle and adapter assemblies 100, 200, as described in greater detail below.

As seen in FIGS. 17-24, to secure adapter assembly 200 to handle assembly 100, components of proximal housing 200*a* of adapter assembly 200 are aligned with components of handle mount 112 so that handle and adapter assemblies 100, 200 can be coupled upon approximation thereof. In particular, alignment pin 112*c* of handle mount 112 of handle assembly 100 is received in alignment bore 204 of proximal housing 200*a* of adapter assembly 200 and first, second, and third output assemblies 130*a*, 130*b*, 130*c* of handle assembly 100 are received within first, second, and third input couplers 210*a*, 210*b*, 210*c* of adapter assembly 200, respectively. Further, angled surfaces 206*c* of spring loaded button 206 of adapter assembly 200 cam along tapered distal surfaces 112*e* of engagement teeth 112*d* of handle mount 112 as spring 208 (FIG. 14) of spring loaded button 206 compresses downwardly toward a compressed state. As ejector pin 202 contacts a compression wall 112*g* (see FIG. 20) of handle mount 112, spring 202*a* of ejector pin 202 compresses toward its compressed state. As nubs 206*a*, 206*b* of spring loaded button 206 cam past engagement teeth 112*d* of handle mount 112, spring 208 of spring loaded button 206 biases toward its uncompressed state so that nubs 206*a*, 206*b* of spring loaded button 206 can be received within first and second windows 112*a*, 112*b* of handle mount 112, respectively. With nubs 206*a*, 206*b* of spring loaded button 206 engaged with shoulders 112*f* of handle mount 112, spring bias forces imparted by spring 202*a* of ejector pin 202, in its compressed state, further bolster engagement by increasing contact forces between nubs 206*a*, 206*b* of spring loaded button 206 and shoulders 112*f* of handle mount 112 to enable adapter and handle assemblies 200, 100 to remain secured together.

To decouple handle and adapter assemblies 100, 200 from one another, spring loaded button 206 is depressed to release nubs 206*a*, 206*b* from shoulders 112*f* of handle mount 112 so that compression forces imparted by spring 202*a* of ejector pin 202 separate handle and adapter assemblies 100, 200 as spring 202*a* biases ejector pin 202 toward its initial extended state (e.g., uncompressed).

Figure 25:
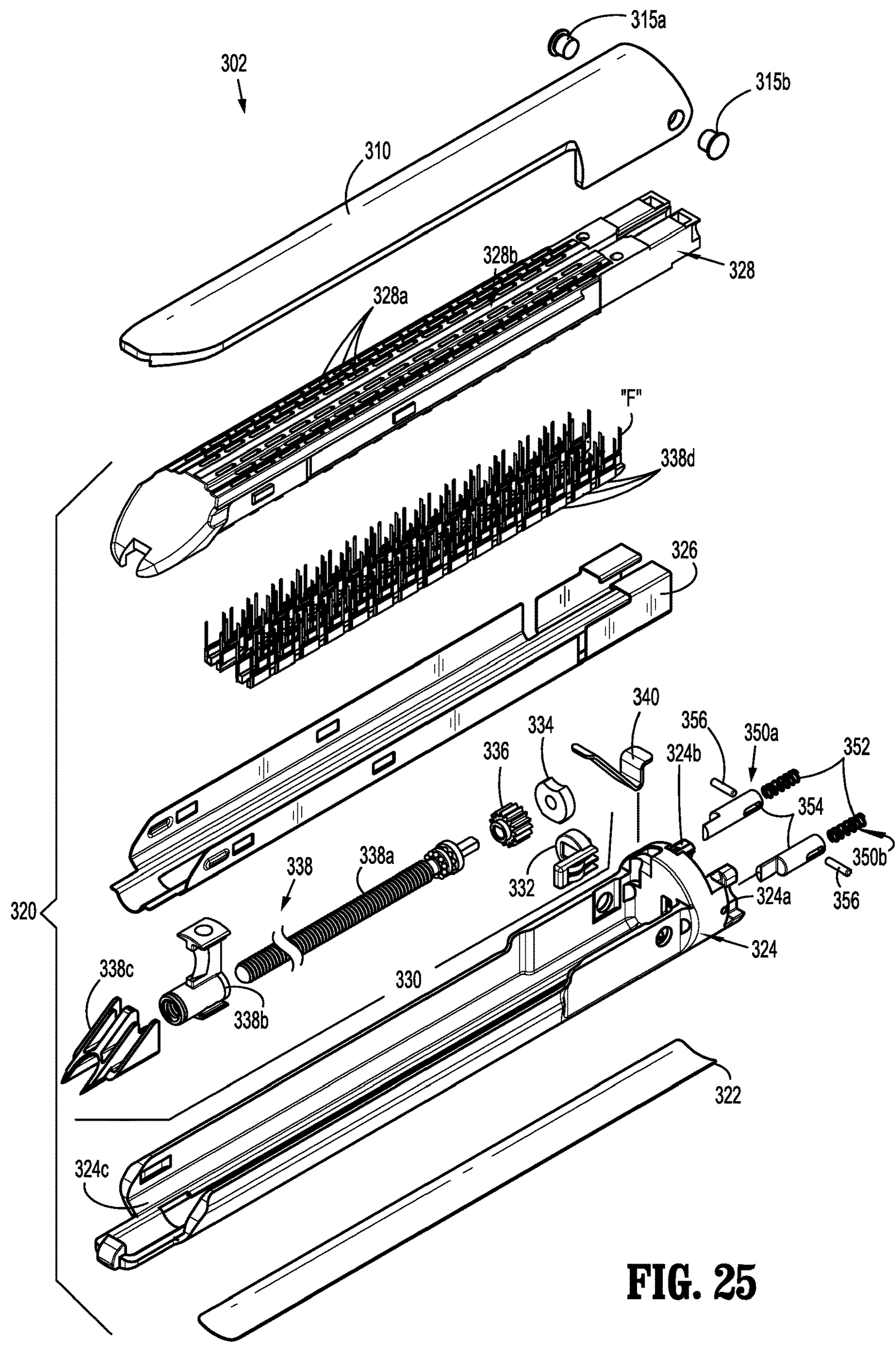
FIG. 25 is a perspective view, with parts separated, of an exemplary end effector of the exemplary loading unit shown in FIG. 1.

Turning now to FIG. 25, an exemplary end effector 302 includes anvil 310 and cartridge assembly 320 that are pinned together by a pair of pins 315*a*, 315*b* and movable between open and closed conditions. Anvil 310 and cartridge assembly 320 cooperate to apply a plurality of linear rows of fasteners "F" (e.g., staples). In certain embodiments, the fasteners are of various sizes, and, in certain embodiments, the fasteners have various lengths or rows (e.g., about 30, 45 and 60 mm in length).

Cartridge assembly 320 includes a base 322 secured to a mounting portion 324, a frame portion 326, and a cartridge portion 328 defining a plurality of fastener retaining slots 328*a* and a knife slot 328*b* in a tissue engaging surface thereof. Mounting portion 324 has mating surfaces 324*a*, 324*b* on a proximal end thereof and defines a receiving channel 324*c* therein that supports frame portion 326, cartridge portion 328, and a fastener firing assembly 330 therein. Cartridge assembly 320 supports a biasing member 340 that engages anvil 310.

Fastener firing assembly 330 includes an electrical contact member 332 in electrical communication with handle assembly 100 (FIG. 1), a bearing member 334, a gear member 336, and a screw assembly 338. Screw assembly 338 includes a lead screw 338*a*, a drive beam 338*b*, and an actuation sled 338*c* that is engagable with a plurality of pusher members 338*d*.

Cartridge assembly 320 also supports a pair of plunger assemblies 350*a*, 350*b*. Each of the pair of plunger assemblies 350*a*, 350*b* includes a spring 352, a plunger 354, and a pin 356 that secures each plunger assembly to mounting portion 324. Plunger assemblies 350*a*, 350*b* cooperate with the proximal end of cartridge portion 328 to facilitate securement of cartridge portion 328 within mounting portion 324.

Figures 26A, 26B:
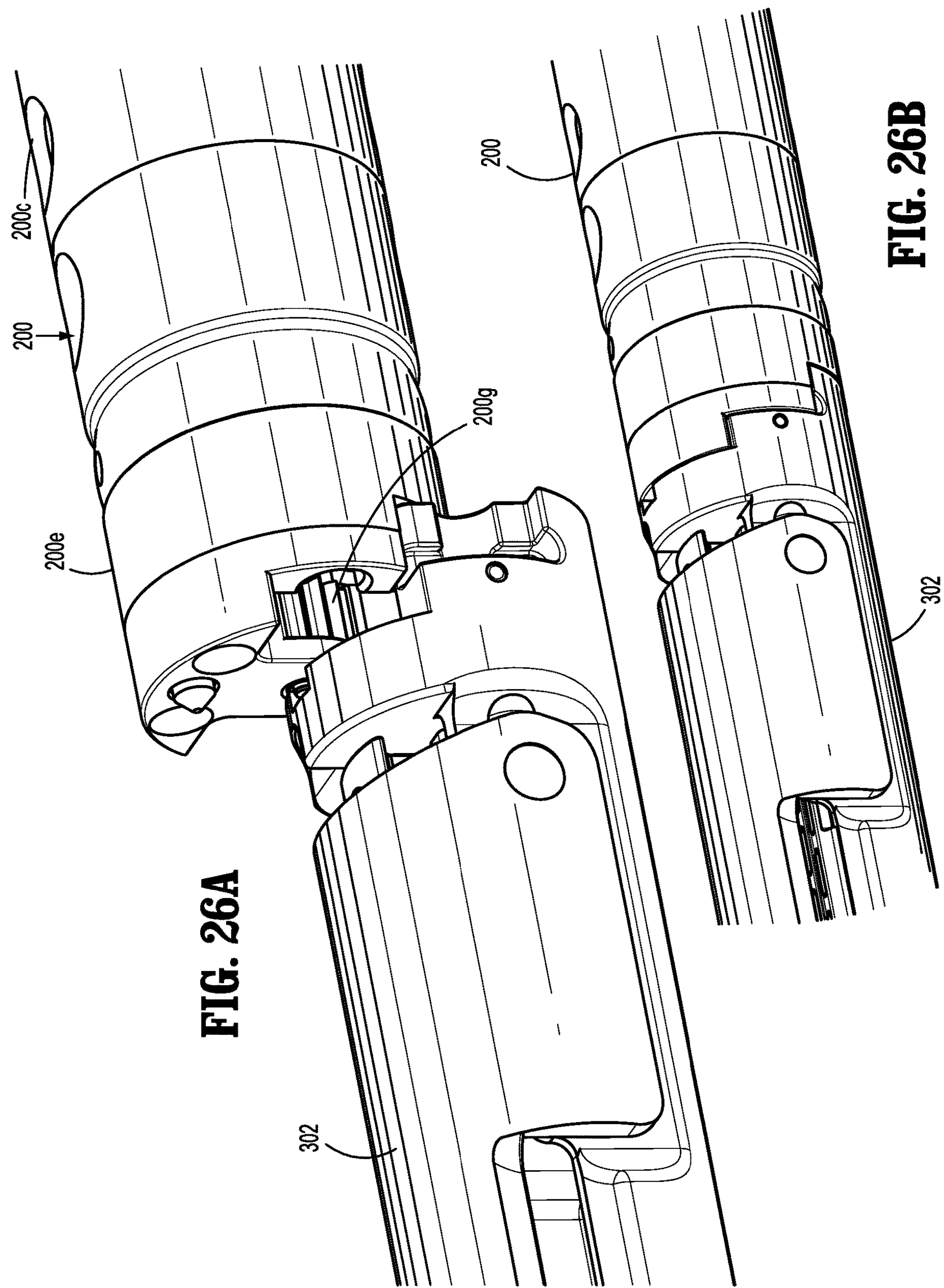
FIGS. 26A and 26B are progressive views illustrating the exemplary end effector of FIG. 25 being attached to the electromechanical surgical system of FIG. 1.

As seen in FIGS. 26A and 26B, adapter assembly 200 can include a distal coupling member 200*e* having a distal gear 200*g* and secured to a distal end of outer tube 200*c*. Coupling member 200*e* and distal gear 200*g* enable end effector 302 to be secured to the distal end of outer tube 200*c*.

For a more detailed description of similar end effectors, coupling members, and components thereof that can be used with, or adapted for use with, the presently described electromechanical surgical system 10, reference can be made to U.S. patent application Ser. No. 14/257,063, filed on Apr. 21, 2014, the entire contents of which are incorporated by reference herein as noted above.

Referring again to FIGS. 1-25, once the components of electromechanical surgical system 10 are coupled together, one or more of actuators 104*a*-104*c* of handle assembly 100 can be manipulated to enable drive assembly 110 of handle assembly 100 to operate loading unit 300 (and/or end effector 302).

Selector motor 128 is actuatable to rotate selector cam 126 between a first position or firing state, a second position or rotation state, and a third position or articulation state. In each of the firing, rotation, and articulation states, one of the first, second, and third output assemblies 130*a*, 130*b*, 130*c* is received within recess 126*d* of selector cam 126 and disposed in an engaged position (e.g., extended) while the other two output assemblies of the first, second, and third output assemblies 130*a*, 130*b*, 130*c* are separated from recess 126*d* of selector cam 126 and disposed in a disengaged position (e.g., compressed).

In the engaged position, engagement key 136 of one respective output assembly of first, second, and third output assemblies 130*a*, 130*b*, 130*c* is extended from output shaft 132 of the respective output assembly so that flanges 136*d*, 136*c* of the respective engagement key 136 are positioned between inner teeth 138*b* of output gear 138 of the respective output assembly and in coupling region 133 of output shaft 132 of the respective output assembly 130*a*.

In the disengaged position, rounded tips 136*a* of engagement keys 136 of two of the output assemblies of first, second, and third output assemblies 130*a*, 130*b*, 130*c* are in contact with, and compressed against, the compression surface 126*f* of selector cam 126 such that flanges 136*d*, 136*c* of the two respective output assemblies are longitudinally offset from, and distal to, inner teeth 138*b* of output gears 138 of the two respective output assemblies.

With teeth 138*a* of output gear 138 of first output assembly 130*a* simultaneously enmeshed with teeth 122*e* of drive gear 122*c*, and teeth 138*a* of output gears 138 of respective second and third output assemblies 130*b*, 130*c*; rotation of drive gear 122*c* rotates all output gears 138 of first, second, and third output assemblies 130*a*, 130*b*, 130*c*. However, only in the engaged position, can the respective output assembly drive the respective driver head 132*i* of the respective output assembly.

To change between the firing, rotation, and articulation states, activation of selector motor 128 rotates selector cam 126 around drive motor assembly 122 such that the one output assembly 130*a*, 130*b*, or 130*c*, in the engaged position, moves to the disengaged position while one of the two disengaged output assemblies 130*a*, 130*b*, and/or 130*c* moves to the engaged position and the other of the two disengaged output assemblies 130*a*, 130*b*, and/or 130*c* moves from a first disengaged position to a second disengaged position. Movement between the engaged and disengaged positions (e.g., one of the output assemblies 130*a*, 130*b*, or 130*c* moves from a disengaged position into an engaged position, and another one of the output assemblies 130*a*, 130*b*, or 130*c* moves from the engaged position into a disengaged position) causes rounded tips 136*a* of respective engagement keys 136 to cam along tapered surfaces 126*e* of recess 126*d* of selector cam 126. Movement of one of the output assemblies from the first disengaged position to the second disengaged position causes rounded tip 136*a* of one of the first, second, and third output assemblies 130*a*, 130*b*, 130*c* to cam along compression surface 126*f* of selector cam 126 while maintaining the respective output assembly in a compressed state.

With respect to the firing state of selector cam 126, first output assembly 130*a* is disposed in the engaged position while second and third assemblies 130*b*, 130*c* are disposed in the disengaged position such that actuator 104*a* can be actuated to fire loading unit 300 (and/or end effector 302). More specifically, depression of actuator 104*a* causes motor 122*a* to rotate drive gear 122*c*. If selector cam 126 is in one of the rotation or articulation states before depressing actuator 104*a*, circuit boards 118*a*, 118*b* of handle assembly 100 communicate with selector motor 128 to rotate selector cam 126 into the firing state, as described above, before actuating motor 122*a* to rotate drive gear 122*c*. Once selector cam 126 is in the firing state, as drive gear 122*c* of drive motor assembly 122 rotates, output gear 138 of first output assembly 130*a* rotates driver head 132*i* of first output assembly 130*a* while output gears 138 of second and third output assemblies 130*b*, 130*c* rotate around their respective output shafts 132 such that driver heads 132*i* of second and third output assemblies 130*b*, 130*c* do not rotate. Rotation of driver head 132*i* of first output assembly 130*a* rotates first input coupler 210*a* of adapter assembly 200 to rotate firing shaft 214. Rotation of firing shaft 214 causes lead screw 338*a* of end effector 302 to rotate and advance drive beam 338*b* and actuation sled 338*c* distally along anvil and cartridge assemblies 310, 320 to fire fasteners "F."

With respect to the rotation state of selector cam 126, second output assembly 130*b* is disposed in the engaged position while first and third output assemblies 130*a*, 130*c* are disposed in the disengaged position such that actuator 104*c* can be rotated to rotate loading unit 300 (and/or end effector 302) about longitudinal axis "L" relative to handle assembly 100. More specifically, rotation of actuator 104*c* causes motor 122*a* to rotate drive gear 122*c*. If selector cam 126 is in one of the firing or articulation states before rotation of actuator 104*c*, circuit boards 118*a*, 118*b* of handle assembly 100 communicate with selector motor 128 to rotate selector cam 126 into the rotation state, as described above, before actuating motor 122*a* to rotate drive gear 122*c*. Once selector cam 126 is in the rotation state, as drive gear 122*c* of drive motor assembly 122 rotates, output gear 138 of second output assembly 130*b* rotates driver head 132*i* of second output assembly 130*b* while output gears 138 of first and third output assemblies 130*a*, 130*c* rotate around their respective output shafts 132 such that driver heads 132*i* of first and third output assemblies 130*a*, 130*c* do not rotate. Rotation of driver head 132*i* of second output assembly 130*b* rotates second input coupler 210*b* of adapter assembly 200 to rotate rotation shaft 218. As rotation shaft 218 rotates, rotation gear 218*a* of rotation shaft 218 turns rotation ring gear 220 and rotates distal housing 200*b* and outer tube 200*c* of adapter assembly 200. Rotation of outer tube 200*c* causes loading unit 300 (and/or end effector 302) to rotate about longitudinal axis "L."

With respect to the articulation state of selector cam 126, third output assembly 130*c* is disposed in the engaged position while first and second output assemblies 130*a*, 130*b* are disposed in the disengaged position such that actuator 104*a* can be moved laterally (e.g., left or right) relative to handle assembly 100 to articulate loading unit 300 (and/or end effector 302) relative to longitudinal axis "L" and relative to handle and adapter assemblies 100, 200. More specifically, lateral movement of actuator 104*a* relative to handle assembly 100 causes motor 122*a* to rotate drive gear 122*c*. If selector cam 126 is in one of the rotation or firing states before laterally moving actuator 104*a*, circuit boards 118*a*, 118*b* of handle assembly 100 communicate with selector motor 128 to rotate selector cam 126 into the articulation state, as described above, before actuating motor 122*a* to rotate drive gear 122*c*. Once selector cam 126 is in the articulation state, as drive gear 122*c* of drive motor assembly 122 rotates, output gear 138 of third output assembly 130*c* rotates driver head 132*i* of third output assembly 130*c* while output gears 138 of first and second output assemblies 130*a*, 130*b* rotate around their respective output shafts 132 such that driver heads 132*i* of first and second output assemblies 130*a*, 130*b* do not rotate. Rotation of driver head 132*i* of third output assembly 130*c* rotates third input coupler 210*c* of adapter assembly 200 to rotate articulation shaft 226. As articulation shaft 226 rotates, articulation sleeve 228 axially slides along longitudinal axis "L" to axially move inner tube 200*d* relative to outer tube 200*c* and cause loading unit 300 (and/or end effector 302) to articulate relative to adapter assembly 200 and longitudinal axis "L."

Any of the components described herein may be fabricated from either metals, plastics, resins, composites or the like taking into consideration strength, durability, wearability, weight, resistance to corrosion, ease of manufacturing, cost of manufacturing, and the like.

It is also contemplated that any of the rotatable components described herein can be rotated in clockwise and/or counterclockwise directions about their respective longitudinal axes.

In embodiments, any of the components described herein, such as the loading unit and/or adapter, can include one or more microchips, such as, for example a one-wire microchip (e.g., microchip model nos. DS2465, DS28E15, and/or DS2432, available from MAXIM INTEGRATED, San Jose, Calif.) that electrically couple to the circuit board/controller of handle assembly 100. Exemplary one-wire microchips are shown and described in U.S. Pat. No. 6,239,732, the entire contents of which are incorporated by reference herein. Any of these chips can include encrypted authentication (e.g., SULU ID) and/or may be one wire compatible.

The various embodiments disclosed herein may also be configured to work with robotic surgical systems and what is commonly referred to as "Telesurgery." Such systems employ various robotic elements to assist the clinician and allow remote operation (or partial remote operation) of surgical instrumentation. Various robotic arms, gears, cams, pulleys, electric and mechanical motors, etc. may be employed for this purpose and may be designed with a robotic surgical system to assist the clinician during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of clinicians may prep the subject for surgery and configure the robotic surgical system with one or more of the instruments disclosed herein while another clinician (or group of clinicians) remotely control the instruments via the robotic surgical system. As can be appreciated, a highly skilled clinician may perform multiple operations in multiple locations without leaving his/her remote console which can be both economically advantageous and a benefit to the subject or a series of subjects.

The robotic arms of the surgical system are typically coupled to a pair of master handles by a controller. The handles can be moved by the clinician to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the clinician. The scale factor or gearing ratio may be adjustable so that the operator can control the resolution of the working ends of the surgical instrument(s).

The master handles may include various sensors to provide feedback to the clinician relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the clinician with enhanced tactile feedback simulating actual operating conditions. The master handles may also include a variety of different actuators for delicate tissue manipulation or treatment further enhancing the clinician's ability to mimic actual operating conditions.

Figure 27:
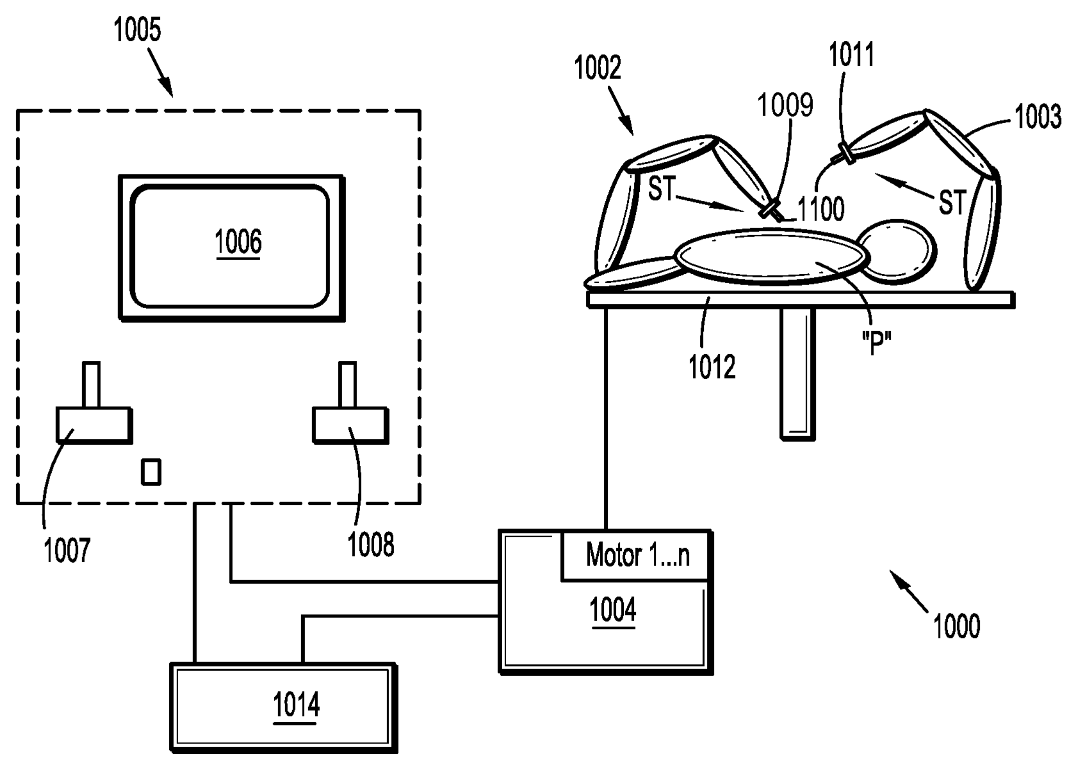
FIG. 27 is a schematic illustration of a medical work station and operating console in accordance with the present disclosure.

Referring to FIG. 27, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a clinician, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical instrument or surgical tool "ST" supporting a loading unit and/or end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a subject "P" lying on a subject table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from subject/living being "P" and/or anatomical atlases.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown or described in connection with certain embodiments may be combined with the elements and features of certain other embodiments without departing from the scope of the present disclosure, and that such modifications and variations are also included within the scope of the present disclosure. Accordingly, the subject matter of the present disclosure is not limited by what has been particularly shown and described.

What is claimed is:

1. An electromechanical surgical system comprising:

a drive motor extending to a drive gear;

a selector cam;

a selector motor extending to a selector gear, the selector gear positioned to move the selector cam between a first position and a second position;

a first output shaft and a first output gear, the first output shaft selectively coupled to the first output gear by a first engagement key, the first output gear rotatable with the drive gear of the drive motor, the first engagement key coupled to the selector cam while the selector cam is in the first position to engage the first output gear with the first output shaft, the first output shaft rotatable with the first output gear in response to rotation of the drive gear of the drive motor while the first output gear is coupled to the first output shaft, the first output gear being rotatable relative to the first output shaft while the selector cam is in the second position; and a second output shaft and a second output gear, the second output shaft selectively coupled to the second output gear by a second engagement key, the second output gear engaged with the first output gear, the second engagement key coupled to the selector cam while the selector cam is in the second position to engage the second output gear with the second output shaft, the second output shaft rotatable with the second output gear in response to rotation of the drive gear of the drive motor while the second output gear is coupled to the second output shaft, the second output gear being rotatable relative to the second output shaft while the selector cam is in the first position.

2. The electromechanical surgical system of claim 1, wherein the first engagement key and the first output shaft are coupled by a first spring, the first spring positioned to bias the first engagement key toward the selector cam.

3. The electromechanical surgical system of claim 2, wherein the selector cam includes a compression surface positioned to urge the first engagement key toward the first output shaft and exert compression forces on the first spring while the first engagement key is in contact with the compression surface of the selector cam.

4. The electromechanical surgical system of claim 1, wherein the first engagement key includes a flange extending therefrom and the first output gear includes inner teeth, wherein the flange of the first engagement key is slidable through a slot defined in the first output shaft between a disengaged position and an engaged position to selectively engage the first output gear with the first output shaft, and wherein in the engaged position, the flange of the first engagement key is engaged with the inner teeth of the first output gear and the slot of the first output shaft so that the first output shaft rotates with the first output shaft.

5. The electromechanical surgical system of claim 4, wherein in the disengaged position, the flange of the first engagement key is engaged with the slot of the first output shaft and spaced from the first output gear such that the first output gear rotates relative to the first output shaft.

6. The electromechanical surgical system of claim 1, wherein the selector cam defines a recess including tapered sidewalls, and wherein the first engagement key is configured to cam along the tapered sidewalls of the recess as the selector cam moves between the first and second positions.

7. The electromechanical surgical system of claim 1, wherein the second engagement key and the second output shaft are coupled by a second spring, the second spring positioned to bias the second engagement key toward the selector cam.

8. The electromechanical surgical system of claim 7, wherein the selector cam includes a compression surface positioned to urge the second engagement key toward the second output shaft and exert compression forces on the second spring while the second engagement key is in contact with the compression surface of the selector cam.

9. The electromechanical surgical system of claim 1, wherein the second engagement key includes a flange extending therefrom and the second output gear includes inner teeth, wherein the flange of the second engagement key is slidable through a slot defined in the second output shaft between a disengaged position and an engaged position to selectively engage the second output gear with the second output shaft, and wherein in the engaged position, the flange of the second engagement key is engaged with the inner teeth of the second output gear and the slot of the second output shaft so that the second output shaft rotates with the second output shaft.

10. The electromechanical surgical system of claim 9, wherein in the disengaged position, the flange of the second engagement key is engaged with the slot of the second output shaft and spaced from the second output gear such that the second output gear rotates relative to the second output shaft.

11. The electromechanical surgical system of claim 1, wherein the second engagement key includes a rounded tip configured to cam along the selector cam as the selector cam moves between the first and second positions.

12. The electromechanical surgical system of claim 1, further including a third output shaft and a third output gear, the third output shaft selectively coupled to the third output gear by a third engagement key, the third output gear engaged with the first output gear, the third engagement key positionable within the selector cam while the selector cam is in a third position to engage the third output gear with the third output shaft, the third output shaft rotatable with the third output gear in response to rotation of the drive gear of the drive motor while the third output gear is engaged with the third output shaft, the third output gear being rotatable relative to the third output shaft while the selector cam in is in the first and second positions.

13. The electromechanical surgical system of claim 12, wherein the third engagement key and the third output shaft are coupled by a third spring, the third spring positioned to bias the third engagement key toward the selector cam.

14. The electromechanical surgical system of claim 13, wherein the selector cam includes a compression surface positioned to urge the third engagement key toward the third output shaft and exert compression forces on the third spring.

15. The electromechanical surgical system of claim 12, wherein the third engagement key includes a flange extending therefrom and the third output gear includes inner teeth, wherein the flange of the third engagement key is slidable through a slot defined in the third output shaft between a disengaged position and an engaged position to selectively engage the third output gear with the third output shaft, and wherein in the engaged position, the flange of the third engagement key is engaged with the inner teeth of the third output gear and the slot of the third output shaft such that the third output gear and the third output shaft move together.

16. The electromechanical surgical system of claim 15, wherein in the disengaged position, the flange of the third engagement key is engaged with the slot of the third output shaft and spaced from the third output gear so that the third output gear rotates relative to the third output shaft.

17. An electromechanical surgical system, comprising:

an adapter assembly;

a loading unit coupled to the adapter assembly;

a surgical device coupled to the adapter assembly, the surgical device including:

a drive motor;

a drive gear coupled to the drive motor;

a selector cam;

a selector motor extending to a selector gear, the selector gear positioned to move the selector cam between a first position and a second position;

a first output shaft and a first output gear, the first output gear rotatable with the drive gear of the drive motor, the first output shaft rotatable with the first output gear while the selector cam is in the first position; and a second output shaft and a second output gear, the second output gear engaged with the first output gear, the second output shaft rotatable with the second output gear while the selector cam is in the second position.

18. The electromechanical surgical system of claim 17, wherein at least one of the first and second output shafts is selectively coupled to a respective one of the first and second output gears by an engagement key.

19. The electromechanical surgical system of claim 17, wherein the adapter assembly is removably coupled to the surgical device by at least one of: a spring loaded button or a spring loaded ejector pin.

20. An electromechanical surgical system, comprising:

an adapter assembly including first and second input couplers;

a loading unit removably coupled to the adapter assembly and operably coupled to the first and second input couplers of the adapter assembly; and a surgical device coupled to the adapter assembly, the surgical device including:

a drive motor;

a drive gear coupled to the drive motor;

a selector cam;

a selector motor extending to a selector gear, the selector gear positioned to move the selector cam between a first position and a second position;

a first output gear rotatable with the drive gear of the drive motor;

a first output shaft rotatable with the first output gear and coupled to the first input coupler of the adapter assembly to drive the first input coupler while the selector cam is in the first position;

a second output gear engaged with the first output gear; and a second output shaft rotatable with the second output gear and coupled to the second input coupler of the adapter assembly to drive the second input coupler while the selector cam is in the second position.

* * * * *